US012797354B2

(12) United States Patent
Xiang et al.

(10) Patent No.: US 12,797,354 B2
(45) **Date of Patent: *Nov. 17, 2026**

(54) PHARMACEUTICAL COMPOSITIONS AND PHARMACOKINETICS OF A GAMMA-HYDROXYBUTYRIC ACID DERIVATIVE

(71) Applicant: XWPHARMA LTD., Redwood City, CA (US)

(72) Inventors: William W. Xiang, Fremont, CA (US); Jia-Ning Xiang, Fremont, CA (US); Daniel M. Canafax, Half Moon Bay, CA (US)

(73) Assignee: XWPharma Ltd., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/533,982

(22) Filed: Dec. 8, 2023

(65) Prior Publication Data

US 2024/0130996 A1 Apr. 25, 2024

Related U.S. Application Data

(63) Continuation of application No. 17/383,253, filed on Jul. 22, 2021, now Pat. No. 11,896,573.

(60) Provisional application No. 63/059,514, filed on Jul. 31, 2020, provisional application No. 63/056,141, filed on Jul. 24, 2020.

(51) Int. Cl.

| | |
|---|---|
| ***A61K 31/223*** | (2006.01) |
| ***A61K 9/00*** | (2006.01) |
| ***A61K 9/08*** | (2006.01) |
| ***A61K 9/50*** | (2006.01) |
| ***A61K 31/19*** | (2006.01) |
| ***A61K 47/12*** | (2006.01) |
| ***A61K 47/26*** | (2006.01) |

(52) U.S. Cl.

CPC .......... *A61K 31/223* (2013.01); *A61K 9/0053* (2013.01); *A61K 9/08* (2013.01); *A61K 9/5084* (2013.01); *A61K 31/19* (2013.01); *A61K 47/12* (2013.01); *A61K 47/26* (2013.01)

(58) Field of Classification Search

CPC ...... A61K 31/223; A61K 9/0053; A61K 9/08; A61K 9/5084; A61K 31/19; A61K 47/12; A61K 47/26

See application file for complete search history.

(56) References Cited

U.S. PATENT DOCUMENTS

| | | | |
|---|---|---|---|
| 4,370,338 | A | 1/1983 | Mizoule |
| 4,843,093 | A | 6/1989 | Nagai et al. |
| 5,110,797 | A | 5/1992 | Ienaga et al. |
| 5,594,030 | A | 1/1997 | Conte et al. |
| 6,489,350 | B1 | 12/2002 | Benedyk et al. |
| 7,482,429 | B2 | 1/2009 | Albericio et al. |
| 7,521,455 | B2 | 4/2009 | Nagase et al. |
| 7,960,561 | B2 | 6/2011 | Sorensen et al. |
| 8,193,211 | B2 | 6/2012 | Liang et al. |
| 8,529,954 | B2 | 9/2013 | Lebon et al. |
| 8,591,922 | B1 | 11/2013 | Allphin et al. |
| 8,598,191 | B2 | 12/2013 | Liang et al. |
| 8,765,178 | B2 | 7/2014 | Parikh et al. |
| 8,772,306 | B1 | 7/2014 | Eller |
| 8,778,398 | B2 | 7/2014 | Rourke et al. |
| 9,309,182 | B2 | 4/2016 | Tung et al. |
| 10,272,062 | B2 | 4/2019 | Megret et al. |
| 10,398,662 | B1 | 9/2019 | Allphin et al. |
| 10,457,627 | B2 | 10/2019 | Xiang et al. |
| 10,501,401 | B2 | 12/2019 | Xiang et al. |
| 10,517,832 | B2 | 12/2019 | Shmeis et al. |
| 10,640,451 | B2 | 5/2020 | Xiang et al. |
| 10,774,031 | B2 | 9/2020 | Xiang et al. |
| 10,813,885 | B1 | 10/2020 | Allphin et al. |
| 10,959,956 | B2 | 3/2021 | Allphin et al. |
| 10,966,931 | B2 | 4/2021 | Allphin et al. |
| 10,987,310 | B2 | 4/2021 | Allphin et al. |
| 11,065,224 | B2 | 7/2021 | Megret et al. |
| 11,077,079 | B1 | 8/2021 | Allphin et al. |
| 11,090,269 | B1 | 8/2021 | Allphin et al. |
| 11,147,782 | B1 | 10/2021 | Allphin et al. |
| 11,207,270 | B2 | 12/2021 | Allphin et al. |
| 11,207,276 | B2 | 12/2021 | Shah et al. |
| 11,395,801 | B2 | 7/2022 | Karaborni et al. |
| 11,504,347 | B1 | 11/2022 | Grassot et al. |
| 11,583,510 | B1 | 2/2023 | Grassot et al. |
| 11,602,512 | B1 | 3/2023 | Dubow et al. |
| 11,602,513 | B1 | 3/2023 | Dubow et al. |

(Continued)

FOREIGN PATENT DOCUMENTS

| | | |
|---|---|---|
| AU | 2014/202306 | 5/2014 |
| CN | 1422278 | 6/2003 |

(Continued)

OTHER PUBLICATIONS

Non-Final Office Action for U.S. Appl. No. 17/687,160 mailed on Dec. 4, 2023, 12 pages.

(Continued)

*Primary Examiner* — Shirley V Gembeh
*Assistant Examiner* — Olga V. Tcherkasskaya
(74) *Attorney, Agent, or Firm* — Sheppard Mullin Richter & Hampton LLP

(57) ABSTRACT

Pharmaceutical compositions of 4-((L-valyl)oxy)butanoic acid and the pharmacokinetics of 4-((L-valyl)oxy)butanoic acid and γ-hydroxybutyric acid following oral administration of the pharmaceutical compositions to healthy subjects are disclosed.

11 Claims, 16 Drawing Sheets

(56) References Cited

U.S. PATENT DOCUMENTS

| | | | |
|---|---|---|---|
| 2004/0092455 | A1 | 5/2004 | Mamelak et al. |
| 2004/0214755 | A1 | 10/2004 | Albericio et al. |
| 2005/0182045 | A1 | 8/2005 | Nagase et al. |
| 2005/0220873 | A1 | 10/2005 | Han et al. |
| 2006/0018964 | A1 | 1/2006 | Combessis et al. |
| 2006/0122383 | A1 | 6/2006 | Zhou et al. |
| 2006/0210630 | A1 | 9/2006 | Liang et al. |
| 2007/0134315 | A1 | 6/2007 | Viera et al. |
| 2007/0190145 | A1 | 8/2007 | Venkatesh et al. |
| 2007/0264323 | A1 | 11/2007 | Shojaei et al. |
| 2008/0175873 | A1 | 7/2008 | Zhou et al. |
| 2010/0029771 | A1 | 2/2010 | Ameisen |
| 2010/0047343 | A1 | 2/2010 | Haslam et al. |
| 2010/0144869 | A1 | 6/2010 | Nudelman et al. |
| 2011/0111027 | A1 | 5/2011 | Rourke et al. |
| 2011/0178068 | A1 | 7/2011 | Almarsson et al. |
| 2011/0293729 | A1 | 12/2011 | Lebon et al. |
| 2012/0076865 | A1 | 3/2012 | Allphin et al. |
| 2012/0115950 | A1 | 5/2012 | Mickle et al. |
| 2012/0122952 | A1 | 5/2012 | Tung |
| 2012/0202879 | A1 | 8/2012 | Cook et al. |
| 2012/0282335 | A1 | 11/2012 | Venkatesh et al. |
| 2012/0283300 | A1 | 11/2012 | Kim et al. |
| 2013/0012565 | A1 | 1/2013 | Tung et al. |
| 2013/0143965 | A1 | 6/2013 | Cook et al. |
| 2014/0004202 | A1 | 1/2014 | Suplie et al. |
| 2014/0037745 | A1 | 2/2014 | Liang et al. |
| 2014/0171505 | A1 | 6/2014 | Allphin et al. |
| 2014/0249222 | A1 | 9/2014 | Eller |
| 2014/0271896 | A1 | 9/2014 | Shmeis et al. |
| 2015/0202588 | A1 | 7/2015 | Allphin |
| 2015/0210624 | A1 | 7/2015 | Tung et al. |
| 2016/0015662 | A1 | 1/2016 | Eller |
| 2016/0052862 | A1 | 2/2016 | Frost et al. |
| 2016/0068463 | A1 | 3/2016 | Peoples et al. |
| 2016/0166529 | A1 | 6/2016 | Mahjour et al. |
| 2018/0021284 | A1 | 1/2018 | Megret et al. |
| 2018/0042855 | A1 | 2/2018 | Rourke et al. |
| 2018/0155266 | A1 | 6/2018 | Tung |
| 2018/0193277 | A1 | 7/2018 | Suplie et al. |
| 2018/0318222 | A1 | 11/2018 | Allphin et al. |
| 2019/0021997 | A1 | 1/2019 | Tung |
| 2019/0183806 | A1 | 6/2019 | Guillard |
| 2019/0183836 | A1 | 6/2019 | Megret et al. |
| 2019/0263043 | A1 | 8/2019 | Bhushan et al. |
| 2019/0269640 | A1 | 9/2019 | Megret et al. |
| 2019/0269641 | A1 | 9/2019 | Megret et al. |
| 2019/0282523 | A1 | 9/2019 | Huang |
| 2019/0282532 | A1 | 9/2019 | Megret et al. |
| 2020/0009076 | A1 | 1/2020 | Patel et al. |
| 2020/0039917 | A1 | 2/2020 | Xiang et al. |
| 2020/0113840 | A1 | 4/2020 | Allphin et al. |
| 2020/0113853 | A1 | 4/2020 | Allphin et al. |
| 2020/0114015 | A1 | 4/2020 | Thottathil |
| 2020/0197347 | A1 | 6/2020 | Megret et al. |
| 2020/0223783 | A1 | 7/2020 | Xiang et al. |
| 2020/0276142 | A1 | 9/2020 | Grassot et al. |
| 2020/0330393 | A1 | 10/2020 | Walsh et al. |
| 2020/0360293 | A1 | 11/2020 | Guillard |
| 2020/0360319 | A1 | 11/2020 | Grassot et al. |
| 2020/0368187 | A1 | 11/2020 | Grassot et al. |
| 2021/0069105 | A1 | 3/2021 | Jain et al. |
| 2021/0069136 | A1 | 3/2021 | Jain et al. |
| 2021/0267928 | A1 | 9/2021 | Megret et al. |
| 2021/0393529 | A1 | 12/2021 | Karaborni et al. |
| 2021/0393537 | A1 | 12/2021 | Karaborni et al. |
| 2022/0023247 | A1 | 1/2022 | Xiang et al. |
| 2022/0105044 | A1 | 4/2022 | Karaborni et al. |
| 2022/0160640 | A1 | 5/2022 | Walsh et al. |
| 2022/0304969 | A1 | 9/2022 | Canafax et al. |

FOREIGN PATENT DOCUMENTS

| | | | |
|---|---|---|---|
| CN | 101511388 | | 8/2009 |
| CN | 102076342 | | 5/2011 |
| CN | 102834098 | | 12/2012 |
| CN | 103370289 | | 10/2013 |
| EP | 0635265 | | 1/1995 |
| EP | 1679076 | A1 | 12/2006 |
| EP | 1749525 | | 2/2007 |
| EP | 2566462 | | 3/2013 |
| EP | 2023900 | | 12/2014 |
| FR | 2662695 | | 12/1991 |
| IN | 26/2007 | | 6/2007 |
| IN | 31/2016 | | 7/2016 |
| JP | 62-270552 | | 11/1987 |
| JP | 2002-503673 | | 2/2002 |
| JP | 2003-522198 | | 7/2003 |
| JP | 2004-059452 | | 2/2004 |
| JP | 2008-526713 | | 7/2008 |
| JP | 2013-516465 | | 5/2013 |
| RU | 2142800 | | 12/1999 |
| TW | 201718456 | | 6/2017 |
| WO | 1999/041275 | | 8/1999 |
| WO | 1999/051613 | | 10/1999 |
| WO | 2002/089775 | A1 | 11/2002 |
| WO | 2004/087169 | | 10/2004 |
| WO | 2004/087169 | A1 | 10/2004 |
| WO | 2005/034923 | A1 | 4/2005 |
| WO | 2005/123731 | | 12/2005 |
| WO | 2008/033351 | | 3/2008 |
| WO | 2006/038226 | | 4/2009 |
| WO | 2009/040331 | | 4/2009 |
| WO | 2009/102462 | | 8/2009 |
| WO | 2009/137717 | | 11/2009 |
| WO | 2009/147681 | | 12/2009 |
| WO | 2010/124046 | | 10/2010 |
| WO | 2011/119839 | | 9/2011 |
| WO | 2011/139271 | A1 | 11/2011 |
| WO | 2013/019561 | | 2/2013 |
| WO | 2013/163244 | | 10/2013 |
| WO | 2014/031840 | | 2/2014 |
| WO | 2014/078014 | | 5/2014 |
| WO | 2014/152263 | | 9/2014 |
| WO | 2014/205393 | | 12/2014 |
| WO | 2015/057884 | | 4/2015 |
| WO | 2015/083129 | | 6/2015 |
| WO | 2015/166473 | | 11/2015 |
| WO | 2017/049470 | | 3/2017 |
| WO | 2017/050259 | | 3/2017 |
| WO | 2018/015563 | | 1/2018 |
| WO | 2018/098472 | | 5/2018 |
| WO | 2020/106735 | | 5/2020 |

OTHER PUBLICATIONS

Notice of Allowance for U.S. Appl. No. 17/974,316 mailed on Nov. 20, 2023, 10 pages.

International Search Report and Written Opinion for International Application No. PCT/CN2016/099763, mailed on Jan. 3, 2017, 15 pages.

International Search Report and Written Opinion for International Application No. PCT/CN2017/078873, mailed on Jan. 9, 2018, 12 pages.

International Search Report and Written Opinion for International Application No. PCT/CN2018/090151, mailed on Feb. 20, 2019, 14 pages.

International Search Report and Written Opinion for International Application No. PCT/CN2018/097241, mailed on Apr. 28, 2019, 11 pages.

International Search Report and Written Opinion for International Application No. PCT/CN2018/109115, mailed on Jul. 8, 2019, 11 pages.

International Search Report and Written Opinion for International Application No. PCT/CN2018/118565, mailed on Jul. 8, 2019, Apr. 28, 2019, 13 pages.

International Search Report and Written Opinion for International Application No. PCT/US2020/066047, mailed on Mar. 23, 2021, 11 pages.

International Preliminary Report on Patentability for PCT Application No. PCT/US2020/066047, dated May 17, 2022, 5 pages.

(56) References Cited

OTHER PUBLICATIONS

Partial International Search Report and Written Opinion for PCT Application No. PCT/US2021/037830, mailed on Oct. 6, 2021, 14 pages.
International Search Report and Written Opinion for PCT Application No. PCT/US2021/037830, mailed on Dec. 7, 2021, 20 pages.
International Preliminary Report on Patentability for Application No. PCT/US2021/037830, mailed on Dec. 29, 2022, 12 pages.
Partial International Search Report and Written Opinion for PCT Application No. PCT/US2021/037909, mailed on Oct. 4, 2021, 26 pages.
International Search Report and Written Opinion for PCT Application No. PCT/US2021/037909, mailed on Dec. 2, 2021, 27 pages.
International Preliminary Report on Patentability for Application No. PCT/US2021/037909, mailed on Dec. 29, 2022, 17 pages.
International Search Report and Written Opinion for PCT Application No. PCT/US2021/042818, mailed on Nov. 12, 2021, 13 pages.
International Search Report and Written Opinion for PCT Application No. PCT/US2021/042818, mailed on Jan. 11, 2022, 18 pages.
International Preliminary Report on Patentability for Application No. PCT/US2021/042818, mailed on Feb. 2, 2023, 11 pages.
International Search Report and Written Opinion for PCT Application No. PCT/US2021/053640, mailed on Mar. 3, 2022, 18 pages.
International Preliminary Report on Patentability for PCT Application No. PCT/US2021/053640, dated Mar. 28, 2023.
International Search Report and Written Opinion for PCT Application No. PCT/US2022/020926, mailed on Jun. 20, 2022, 16 pages.
International Preliminary Report on Patentability for PCT Application No. PCT/US2022/020926, mailed on.
Non-final Office Action for U.S. Appl. No. 17/350,478, mailed on Oct. 22, 2021, 19 pages.
Final Office Action for U.S. Appl. No. 17/350,478, mailed on Feb. 7, 2022, 19 pages.
Notice of Allowance for U.S. Appl. No. 17/350,478, mailed on Apr. 14, 2022, 10 pages.
Non-final Office Action for U.S. Appl. No. 17/737,700, mailed on Jan. 31, 2023, 19 pages.
Final Office Action for U.S. Appl. No. 17/737,700, mailed on Jun. 15, 2023, 18 pages.
Non-final Office Action for U.S. Appl. No. 17/350,939, mailed on Oct. 22, 2021, 6 pages.
Final Office Action for U.S. Appl. No. 17/350,939, mailed on Dec. 14, 2021, 7 pages.
Notice of Allowance for U.S. Appl. No. 17/350,939, mailed on Feb. 9, 2022, 8 pages.
Non-final Office Action for U.S. Appl. No. 17/383,253, mailed on Sep. 27, 2022, 14 pages.
Final Office Action for U.S. Appl. No. 17/383,253, mailed on Jan. 18, 2023, 11 pages.
Notice of Allowance for U.S. Appl. No. 17/383,253, mailed on Jun. 1, 2023, 11 pages.
Non-final Office Action for U.S. Appl. No. 17/494,749, mailed on Mar. 4, 2022, 12 pages.
Final Office Action for U.S. Appl. No. 17/494,749, mailed on Apr. 8, 2022, 10 pages.
Notice of Allowance for U.S. Appl. No. 17/494,749, mailed on Jun. 8, 2022, 9 pages.
Non-final Office Action for U.S. Appl. No. 17/843,097, mailed on Jun. 14, 2023, 9 pages.
Non-final Office Action for U.S. Appl. No. 17/698,609, mailed on May 27, 2022, 14 pages.
Final Office Action for U.S. Appl. No. 17/698,609, mailed on Jul. 18, 2022, 14 pages.
Notice of Allowance for U.S. Appl. No. 17/698,609, mailed on Oct. 14, 2022, 9 pages.
Abdul et al., "A flexible technology for modified-release drugs: Multiple-unit pellet system (MUPS)", Journal of Controlled Release, Oct. 2010, vol. 147, No. 1, pp. 2-16.
Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.
Search Report for Australia Application No. 2017406159, mailed on Feb. 28, 2020, 6 pages.
Search Report for Australia Application No. 2016328150, mailed on Mar. 27, 2020, 4 pages.
Search Report for Russia Application No. 2019134607, mailed on Feb. 11, 2020, 7 pages (translation).
Cameo Chemicals, ethyl-3-hydroxybutyrate, retrieved from https://web.archive.org/web/20170209085248/ https://cameochemicals.noaa.gov/chemical/20385, 2017, 5 pages.
Durig et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.
Durig et al., Water-Soluble Cellulose Ethers as Release Modulators for Ethylcellulose Coatings on Multiparticulates, Pharmaceutical Technology Report, Annual Meeting of the American Association of Pharmaceutical Scientists, Oct. 29-Nov. 2, 2006, San Antonio, TX, 9 pages.
Jiang, et al., Copper-Catalyzed Aerobic Oxidative Regioselective Thiocyanation of Aromatics and Heteroaromatics. J. Org. Chem. 2017, 82, 18, 9312-9320.
Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.
Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.
Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.
Lee et al., "Development of an Immunoassay for the Residues of the Herbicide Bensulfuron-Methyl," Journal of Agricultural and Food Chemistry, Mar. 2002, vol. 50, No. 7, p. 1791-1803.
Luengo et al., "Synthesis and Structure-Activity Relationships of Macrocyclic FKBP Ligands", Bioorganic & Medicinal Chemistry Letters, 1994, vol. 4, No. 2, p. 321-324.
Mcgeer et al., "Pharmacologic Approaches to the Treatment of Amyotrophic Lateral Sclerosis", Drug Mechanisms and Targets, 2006, vol. 19, No. 1, p. 31-37.
RN 1243631-58-4, STN entry date Sep. 29, 2010.
CAS No. 128321-03-9, entry dated Jul. 21, 1990, 1 page.
CAS No. 238401-16-6, entry dated Sep. 10, 1999, 21 pages.
STN Columbus, Registry Jul. 21, 1990, 128321-03-09, 81055-72-3.
STN Columbus, Registry Dec. 4, 2015, CAS No. 1822708-15-5.
RN 142229-71-8, STN entry date Jul. 3, 1992.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 1744-22-5, STN entry date Nov. 16, 1984.
RN 326-45-4, STN entry date Nov. 16, 1984.
RN 747353-64-6, STN REG, Sep. 17, 2004.
RN 60176-62-7, STN entry date Nov. 16, 1984.
RN 60176-63-8, STN REG, Nov. 16, 1984.
RN 60388-38-7, STN entry date Nov. 16, 1984.
CAS Registry No. 238401-16-6 entry date Sep. 10, 1999.
Rothweiler, et al., Probing the ATP-Binding Pocket of Protein Kinase DYRK1A with Benzothiazole Fragment Molecules. J. Med. Chem. 2016, 59, 21, 9814-9824.
Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.
Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.

(56) References Cited

OTHER PUBLICATIONS

Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.

Ward et al., "Discovery of an Orally Bioavailable Nki Receptor Antagonist, (2S, 3S)-(2-Methoxy-5-tetrazol-I-ylbenzyl)(2-phenylpiperidin-3-yl)amine (GR203040), with Potent Antiemetic Activity," Journal of Med. Chem., 1995, vol. 38, p. 4985-4992.

PHARMACEUTICAL COMPOSITIONS AND PHARMACOKINETICS OF A GAMMA-HYDROXYBUTYRIC ACID DERIVATIVE

This application is a continuation of U.S. application Ser. No. 17/383,253, filed on Jul. 22, 2021, now allowed, which claims the benefit under 35 U.S.C. § 119(e) of U.S. Provisional Application No. 63/056,141, filed on Jul. 24, 2020, and U.S. Provisional Application No. 63/059,514 filed on Jul. 31, 2020, each of which is incorporated by reference in its entirety.

FIELD

The disclosure relates to pharmaceutical compositions comprising a γ-hydroxybutyric acid derivative and to the pharmacokinetics of a γ-hydroxybutyric acid derivative.

BACKGROUND

γ-Hydroxybutyric acid is known to be effective in treating certain sleep disorders. Sodium oxybate, which is the sodium salt of γ-hydroxybutyric acid, is approved by the United States Food and Drug Administration for the treatment of sudden muscle weakness and excessive daytime sleepiness associated with narcolepsy.

SUMMARY

According to the present invention, pharmaceutical compositions comprise an aqueous solution comprising 4-((L-valyl)oxy)butanoic acid (Compound (1)) or a pharmaceutically acceptable salt thereof:

(1)

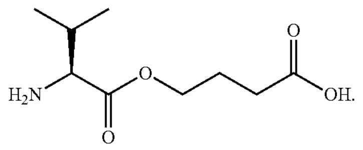

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
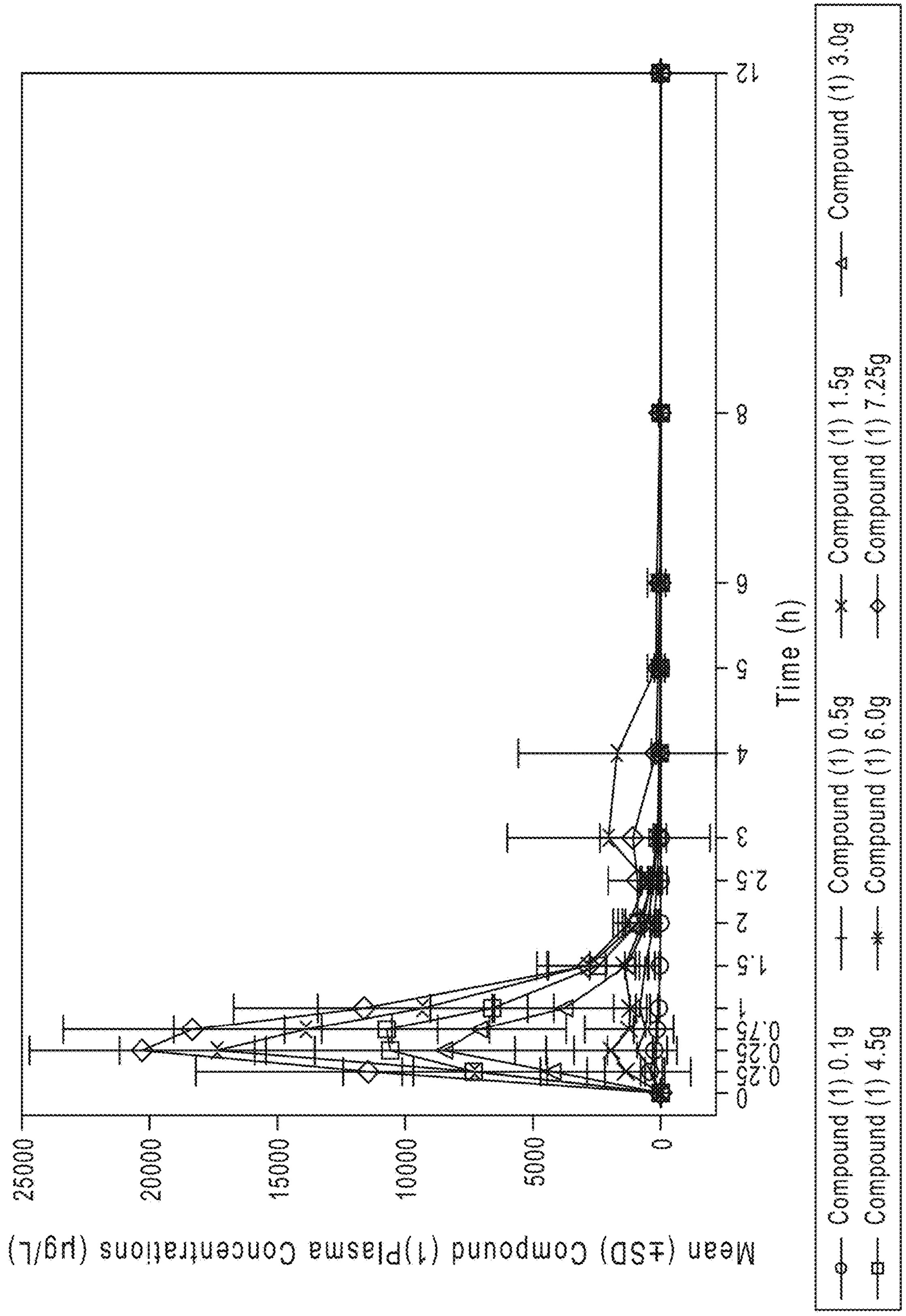
FIG. 1 shows the mean Compound (1) plasma concentration following oral administration of Compound (1) to healthy subjects.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Bioequivalent" refers to a pharmaceutical composition that when administered to a subject or patient, or a population of subjects or patients under the same conditions, exhibits and average maximum γ-hydroxybutyric acid ("GHB") plasma concentration ($C_{max}$), and/or an average GHB plasma area-under-the-curve (AUC) within 89% to 125%.

The term "bioequivalent", as used herein, describes a formulation and/or pharmaceutical composition that is therapeutically equivalent to a reference product when given under the same conditions in a pharmacokinetic evaluation conforming to United States Food and Drug Administration ("USFDA") Guidance on Bioequivalence Testing; regardless of biopharmaceutical class. A value that is "bioequivalent", as used herein, is meant to refer to a pharmacokinetic value (such as the $C_{max}$ or AUC of a formulation described herein) that exhibits substantially similar pharmacokinetic profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence may be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. In some embodiments, a value is bioequivalent to a reference pharmacokinetic value when the geometric mean of the AUC and/or the $C_{max}$ is between 80% and 125% (e.g., at 90% confidence interval) of the reference pharmacokinetic value "Functional coatings" include immediate release coatings, controlled release coatings, modified release coatings, sustained release coatings, pH-release coatings, pulsatile release coatings, timed-release coatings, and delayed release coatings. A functional coating is configured to provide a desired property to the granulation comprising 4-((L-valyl)oxy)butanoic acid such as a desired release profile in the gastrointestinal tract following oral administration.

"Immediate release" refers to a pharmaceutical composition that releases substantially all of a pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions include controlled release formulations, delayed release formulations, extended release formulations, sustained release formulations, timed release formulations, pulsatile release formulations, and pH-dependent release formulations. These formulations are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The United States Pharmacopeia ("USP") defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

"Sustained release" pharmaceutical compositions and coating provide for a dissolution rate over an extended period of time following oral administration. Granulations comprising granules having a sustained release coating can be referred to as sustained release granulations. A pharmaceutical composition comprising a sustained release granulation can be referred to as a sustained release pharmaceutical composition.

"pH-Release" pharmaceutical compositions and coatings provide for an increased dissolution rate at an intended pH.

"Pulsatile release" pharmaceutical compositions and coatings exhibit an increased dissolution rate at intervals, where the release intervals can be determined by time, exposure to internal stimuli, or exposure to external stimuli. Examples of pulsatile-release systems include capsular systems, osmotic systems, systems having erodible membranes, and systems having a rupturable coating. Examples of stimuli include temperature, chemicals, electrical stimuli, and magnetic stimuli.

"Timed-release" pharmaceutical compositions and coatings have a dissolution rate that is a function of time. A time-release pharmaceutical composition or coating includes, for example, delayed release, sustained release, and extended release pharmaceutical compositions and coatings.

"Delayed release" pharmaceutical compositions and coatings provide for an increased dissolution rate at an intended time after administration.

"Dose proportional" refers to a relationship in which an increase in an administered dose is accompanied by proportional increases in a characteristic parameter of the pharmacokinetic ("PK") profile, such as the AUC or $C_{max}$.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically active ingredient" refers to an active drug substance or a compound that is converted following administration into an active drug substance such as a prodrug.

"Prodrug" refers to a derivative of a drug molecule that requires a transformation within the body to provide the active drug. Prodrugs are frequently, although not necessarily, pharmacologically inactive until converted to the parent drug. Prodrugs may be obtained by bonding a promoiety (defined herein) typically via a functional group, to a drug.

"Subject" refers to a healthy human.

"Curing" a disease refers to eliminating a disease or disorder or eliminating a symptom of a disease or disorder.

"Treating" or "treatment" of a disease or disorder refers to reducing the severity of one or more clinical symptom of the disease or disorder, delaying the onset of one or more clinical symptoms of the disease or disorder, and/or mitigating one or more clinical symptoms of the disease or disorder, "Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, and/or stabilization of the disease or disorder or one or more clinical symptoms of the disease or disorder, "Treating" or "treatment" of a disease or disorder refers to producing a clinically beneficial effect without curing the underlying disease or disorder.

"Therapeutically effective amount" refers to the amount of a compound such as pharmaceutically active ingredient that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

"Percent weight gain" or "% wg" such as in a "35% wg" coating refers to a coated granule or granulation in which the weight of the coated granules or granulation is 35% greater than the weight of the uncoated granule or uncoated granulation.

Dissolution profiles were measured using a USP Type 2 dissolution apparatus with a sodium acetate buffered solution at pH 4.5, a temperature of 37° C. and a paddle speed of 75 rpm.

"$C_{max}$" refers to the maximum plasma concentration.

"$T_{max}$" refers to the time to reach the maximum plasma concentration.

"$AUC_{0\text{-}tlast}$" refers to the area under the plasma concentration-time curve from time 0 to the time of the last quantifiable concentration.

"$AUC_{0\text{-}tlast}$" refers to the area under the plasma concentration-time curve from time 0 to the time of the last quantifiable concentration.

"$AUC_{0\text{-}inf}$" refers to the area under the plasma concentration-time curve from time 0 to infinite time, calculated as the sum of $AUC_{0\text{-}tlast}$ and $C_{last}/\lambda z$.

"$AUC_{0\text{-}tau}$" refers to the area under the plasma concentration-time curve during a dosing interval.

"$\lambda z$" refers to the apparent terminal elimination rate constant.

"$T_{1/2}$" refers to the elimination half-life associated with the terminal slope ($\lambda z$) of the semilogarithmic drug concentration-time curve, calculated as $0.693/\lambda z$.

"CL/F" refers to the apparent total body clearance of a drug from the plasma calculated by: $CL/F=Dose/AUC_{0\text{-}inf}$.

Reference is now made to pharmaceutical compositions comprising 4-((L-valyl)oxy)butanoic acid and the pharmacokinetics of 4-((L-valyl)oxy)butanoic acid and γ-hydroxybutyric acid derived in vivo from orally administered 4-((L-valyl)oxy)butanoic acid to healthy subjects. The disclosed pharmaceutical compositions and pharmacokinetics are not intended to be limiting of the claims. To the contrary, the claims are intended to cover all alternatives, modifications, and equivalents.

Sodium oxybate (sodium salt of γ-hydroxybutyric acid, sodium salt of GHB, or Na-GHB) is approved by the United States Food and Drug Administration for the treatment of muscle fatigue and excessive daytime sleepiness associated with narcolepsy. Sodium oxybate is orally administered and is a salt form of the active pharmaceutical ingredient γ-hydroxybutyric acid (GHB). Sodium oxybate contains 0.817 equivalents of γ-hydroxybutyric acid. Sodium oxybate and γ-hydroxybutyric acid have the structure of Formula (2a) and Formula (2b), respectively:

(2a)

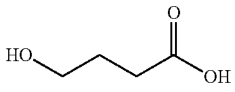

(2b)

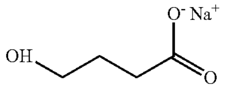

4-((L-Valyl)oxy)butanoic acid (Compound (1)) is a prodrug of γ-hydroxybutyric acid, which following oral administration, is absorbed by the gastrointestinal tract to provide expression "4-((L-valyl)oxy)butanoic acid (1)" with the expression "4-((L-valyl)oxy)butanoic acid (Compound 1)". in the systemic circulation, which is metabolized to provide γ-hydroxybutyric acid in the plasma of a patient. 4-((L-Valyl)oxy)butanoic acid has the structure of Formula (1):

(1)

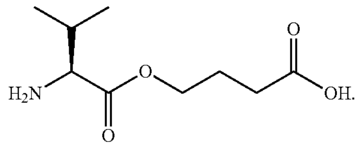

Compound (1) contains 0.512 equivalents of γ-hydroxybutyric acid.

A pharmaceutical composition provided by the present disclosure can comprise an aqueous solution comprising 4-((L-valyl)oxy)butanoic acid (Compound (1)). The aqueous solution can be prepared by dissolving 4-((L-valyl)oxy) butanoic acid as a solid powder or crystalline 4-((L-valyl) oxy)butanoic acid in a aqueous solution, by dissolving granules comprising 4-((L-valyl)oxy)butanoic acid in an aqueous solution, or by dissolving coated granules comprising 4-((L-valyl)oxy)butanoic acid in an aqueous solution where the coating comprises an immediate release coating or a seal coating.

An aqueous solution can comprise 4-((L-valyl)oxy)butanoic acid, a buffer, a sweeting agent, and a flavoring agent.

An aqueous solution provided by the present disclosure can comprise, for example, from 82 wt % to 92 wt % of expression "4-((L-valyl)oxy)butanoic acid (1)" with the expression "4-((L-valyl)oxy)butanoic acid (Compound 1)";

from 5 wt % to 9 wt % of a pH adjusting agent;

from 3 wt % to 7 wt % of a sweetening agent; and from 0.2 wt % to 0.6 wt % of a flavoring agent; wherein, wt % is based on the total solids weight of the pharmaceutical composition.

An aqueous solution provided by the present disclosure can comprise, for example, from 85 wt % to 89 wt % of expression "4-((L-valyl)oxy)butanoic acid (1)" with the expression "4-((L-valyl)oxy)butanoic acid (Compound 1)";

from 6 wt % to 8 wt % of a pH adjusting agent;

from 4 wt % to 6 wt % of a sweetening agent; and from 0.3 wt % to 0.5 wt % of a flavoring agent; wherein, wt % is based on the total solids weight of the pharmaceutical composition;

A pH adjusting agent can comprise an acid, such as, for example, malic acid.

An aqueous solution can have a pH, for example, from 4.0 to 5.0, from 4.2 to 4.8, or from 4.3 to 4.7.

A sweetening agent can comprise any suitable sweeting agent. Examples of suitable sweetening agents include acesulfame potassium, alitame, aspartame, dextrose, erythritol, fructose, glucose, lactitol, maltitol, maltose, mannitol, neohesperidin dihydrochalcone, neotame, saccharin, sodium cyclamate, sorbitol, sucralose, sucrose, compressible sugar, confectioner's sugar, tagatose, thaumatin, and xylitol.

A sweetening agent can compose sucralose.

A flavoring can comprise any suitable flavoring. A flavoring can comprise strawberry essence.

An aqueous solution provided by the present disclosure can have a solids concentration, for example, from 80 mg/mL to 120 mg/mL, from 90 mg/mL to 110 mg/mL, or from 95 mg/mL to 105 mg/mL.

An aqueous solution provided by the present disclosure can comprise, for example, from 2 g to 20 g of expression "4-((L-valyl)oxy)butanoic acid (1)" with the expression "4-((L-valyl)oxy)butanoic acid (Compound 1)", from 6 g to 16 g, or from 8 g to 12 g of expression "4-((L-valyl)oxy) butanoic acid (1)" with the expression "4-((L-valyl)oxy) butanoic acid (Compound 1)".

An aqueous solution provided by the present disclosure can comprise, for example, from 2 g-equivalents to 10 g-equivalents of γ-hydroxybutyric acid, from 4 g-equivalents to 8 g-equivalents, or from 8 g-equivalents to 6 g-equivalents of γ-hydroxybutyric acid.

An aqueous solution provided by the present disclosure can be stable within 98% of the initial about of expression "4-((L-valyl)oxy)butanoic acid (1)" with the expression "4-((L-valyl)oxy)butanoic acid (Compound 1)". after 96 hours at 25° C.

Following oral administration of an aqueous solution comprising 7.5 g of 4-((L-valyl)oxy)butanoic acid (1); to a population of fasted subjects the plasma pharmacokinetic profile of γ-hydroxybutyric acid is characterized by:

a mean $T_{1/2}$ from 0.7 hours to 0.9 hours;

a median $T_{max}$ from 0.8 hours to 1.2 hours;

a mean $C_{max}$ from 102 μg/mL to 132 μg/mL; and a mean $AUC_{0\text{-}inf}$ from 333 h×μg/mL to 373 h×μg/mL.

Following oral administration of an aqueous solution comprising 7.5 g of expression "4-((L-valyl)oxy)butanoic acid (1)" with the expression "4-((L-valyl)oxy)butanoic acid (Compound 1)"; to a population of fed subjects the plasma pharmacokinetic profile of γ-hydroxybutyric acid is characterized by:

a mean $T_{1/2}$ from 0.7 hours to 0.9 hours;

a median $T_{max}$ from 1.6 hours to 2.0 hours;

a mean $C_{max}$ from 135 μg/mL to 155 μg/mL; and a mean $AUC_{0\text{-}inf}$ from 330 h×μg/mL to 370 h×μg/mL.

A pharmaceutical composition provided by the present disclosure can comprise a plurality of coated granules, wherein the granules comprise a core and a functional coating overlying and surrounding the core, or uncoated granule.

The coated granules can have an average particle size distribution ("PSD") (D50) from 150 μm to 400 μm, from 150 μm to 350 μm, from 150 μm to 300 μm, or from 150 μm to 250 μm, where PSD is determined by sieve analysis.

A core can comprise greater than 90 wt %, such as greater than 92 wt %, greater than 94 wt %, greater than 96 wt %, greater than 98 wt %, or greater than 99 wt % of expression "4-((L-valyl)oxy)butanoic acid (1)" with the expression "4-((L-valyl)oxy)butanoic acid (Compound 1)", where wt % is based on the total weight of the core. A core can comprise, for example, from 90 wt % to 99.5 wt % expression "4-((L-valyl)oxy)butanoic acid (1)" with the expression "4-((L-valyl)oxy)butanoic acid (Compound 1)", from 92 wt %, to 99 wt %, from 94 wt % to 98 wt %, or from 95 wt % to 98 wt % expression "4-((L-valyl)oxy)butanoic acid (1)" with the expression "4-((L-valyl)oxy)butanoic acid (Compound 1)", where wt % is based on the total weight of the core.

The granules and methods of forming the granules are disclosed in U.S. application Ser. No. 17/350,478 filed on Jun. 17, 2021, which is incorporated by reference in its entirety.

The granules can comprise a coating. A coating can comprise an immediate release coating and/or a functional coating.

An immediate release coating refers to a coating that completely dissolves to release the 4-((L-valyl)oxy)butanoic acid. for example, in less than 10 minutes, less than 8 minutes, less than 6 minutes, less than 5 minutes, or less than 4 minutes, when tested in a USP Type 2 dissolution apparatus in a buffered solution at pH 4.5 at a temperature of 37° C. and a paddle speed of 100 rpm.

Granules comprising a γ-hydroxybutyric acid coating are referred to as coated granules. Coated granules comprising expression "4-((L-valyl)oxy)butanoic acid (1)" with the expression "4-((L-valyl)oxy)butanoic acid (Compound 1)", methods of preparing the coated granules, and properties of the coated granules are disclosed in U.S. application Ser. No. 17/350,939 filed on Jun. 17, 2021, which is incorporated by reference in its entirety.

A coating can have an average thickness, for example, less than 300 μm, less than 200 μm, less than 150 μm, less than 100 μm, less than 50 μm, less than 25 μm, less than 20 μm, less than 10 μm, or less than 5 μm. A coating can have an average thickness, for example, from 5 μm to 300 μm, from 5 μm to 200 μm, from 5 μm to 100 μm, from 5 μm to 50 μm, from 5 μm to 25 μm, from 5 μm to 20 μm, or from 5 μm to 15 μm.

A coated granule can comprise, for example, less than 50 wt % of a coating, less than 40 wt % of a coating, less than 30 wt %, less than 20 wt %, or less than 10 wt % of a coating, where wt % is based on the total weight of the coated granule. Dosage forms containing a highly water-soluble pharmaceutically active ingredient such as Compound (1) can have a thick coating to reduce the release rate of the pharmaceutically active ingredient and/or increase the storage stability of the pharmaceutically active ingredient by minimizing or preventing ingress of moisture.

A coated granule or coated granulation can comprise, for example, greater than 60 wt % of Compound (1), greater than 70 wt %, greater than 80 wt %, or greater than 85 wt % of a pharmaceutically active ingredient, where wt % is based on the total weight of the coated granule or granulation.

A coated granule or granulation comprising a plurality of coated granules can comprise, for example, from 60 wt % to 85 wt % of a pharmaceutically active ingredient, from 65 wt % to 80 wt % or from 70 wt % to 75 wt % of a pharmaceutically active ingredient such as Compound (1), where wt % is based on the total weight of the coated granule or granulation.

A functional coating can comprise an immediate release coating and a coated granule can comprise an immediate release coating. An immediate release granulation comprising coated granules can release greater than 80% of 4-((L-valyl)oxy)butanoic acid, for example, in less than 10 minutes, less than 8 minutes, less than 6 minutes, or less than 4 minutes, when tested in a USP Type 2 dissolution apparatus in a buffered solution at pH 4.5 at a temperature of 37° C. and a paddle speed of 100 rpm. A coated immediate release granulation can comprise a coating comprising a water-soluble polymer such as, for example, hydroxypropylcellulose, polyvinyl alcohol, hydroxypropylmethylcellulose, hydroxypropylethylcellulose, polyvinylpyrrolidone, or polyethyleneglycol.

A functional coating can comprise, for example, a matrix polymer, an anti-static agent, and a plasticizer.

A functional coating can comprise a matrix polymer or combination of matrix polymers. A combination of a matrix polymer and/or a pore forming polymer can be selected to provide for a desired release profile of a pharmaceutically active ingredient in the gastrointestinal tract.

A functional coating can comprise, for example, from 60 wt % to 85 wt % of a matrix polymer, from 65 wt % to 80 wt %, or from 70 wt % to 80 wt %, of a matrix polymer, where wt % is based on the total weight of the functional coating.

A functional coating can comprise, for example, less than 85 wt % of a matrix polymer, less than 80 wt %, less than 75 wt %, less than 70 wt %, or less than 65 wt % of a matrix polymer, where wt % is based on the total weight of the functional coating.

A functional coating can comprise, for example, greater than 60% of a matrix polymer, greater than 65 wt %, greater than 70 wt %, greater than 75 wt %, or greater than 80 wt % of a matrix polymer, where wt % is based on the total weight of the functional coating.

A matrix polymer can comprise a water-insoluble polymer or combination of water-insoluble polymers.

Examples of suitable water insoluble polymers include ethylcellulose and polyvinyl acetates, polyacrylates, and polymethacrylates.

A water insoluble polymer such as ethylcellulose can have an average molecular weight, for example, from 25,000 Daltons, to 300,000 Daltons, such as from 50,000 Daltons to 200,000 Daltons, from 50,000 Daltons to 150,000 Daltons, or from 50,000 Daltons to 100,000 Daltons.

A water insoluble polymer such as ethylcellulose can have a viscosity, for example, less than 100 mPa×sec, less than 75 mPa×sec, less than 50 mPa×sec, less than 25 mPa×sec, less than 20 mPa×sec, or less than 15 mPa×sec, as determined using a Brookfield viscometer in an 80:20 mixture of toluene/ethanol.

Examples of suitable ethylcellulose polymers include ethylcellulose polymers sold under the tradename AQUALON® T10 Pharm, N7 Pharm, N10 Pharm, N14 Pharm, N22 Pharm, N50 Pharm, and N100 Pharm polymers, available from Ashland. Other examples of suitable ethylcellulose polymers include ethylcellulose polymers sold under the tradename ETHOCEL® Standard 7, Standard 10, Standard 14, Standard 20 polymers, available from Dupont.

A matrix polymer can comprise, for example, from 90 wt % to 100 wt % of a water-insoluble polymer, from 91 wt % to 99 wt %, from 82 wt % to 98 wt %, or from 93 wt % to 97 wt % of a water-insoluble polymer, where wt % is based on the total weight of the matrix polymer. A matrix polymer can comprise, for example, greater than 90 wt % of a water insoluble polymer, greater than 92 wt %, greater than 94 wt %, greater than 96 wt %, or greater than 98 wt % of a water insoluble polymer, where wt % is based on the total weight of the matrix polymer. A matrix polymer can comprise, for example, less than 100 wt % of a water insoluble polymer, less than 98 wt %, less than 96 wt %, less than 94 wt %, or less than 92 wt % of a water insoluble polymer, where wt % is based on the total weight of the matrix polymer.

A matrix polymer can comprise a pore forming polymer. Examples of pore forming polymers include water-soluble polymers, polymers that swell or expand such as carbomers, and polymers soluble in gastric fluid such as cellulose acetate phthalate, hydroxypropylcellulose, hydroxypropyl methyl cellulose, methacrylic acid-methyl methacrylate copolymers, and polyvinyl acetate phthalate. A pore forming polymer can increase the permeability of a functional coating under intended conditions.

A matrix polymer can comprise a water-soluble polymer or combination of water-soluble polymers.

Examples of suitable hydroxypropylcellulose polymers include hydroxypropylcellulose polymers sold under the tradename KLUCEL® HF Pharm, MF Pharm, GF Pharm JF Pharm, LF Pharm, EF Pharm, and ELF Pharm polymers, available from Ashland.

Examples of suitable hydroxypropylmethylcellulose polymers include hydroxypropylmethylcellulose polymers sold under the tradename PHARMACOAT® 603, 645, 606 and 615 polymers, available from Shin-Etsu Chemical Co.

A water-soluble polymer such as hydroxypropylcellulose can have an average molecular weight, for example, less than 1,000,000 Daltons, less than 800,000 Daltons, less than 600,000 Daltons, less than 400,000 Daltons, less than 200, 000 Daltons, less than 100,000 Daltons, or less than 50,0000 Daltons.

A water-soluble polymer such as hydroxypropylcellulose can have a viscosity, for example, less than 7,000 mPa×sec, less than 5,000 mPa×sec, less than 3,000 mPa×sec, or less than 1,000 mPa×sec, as determined using a Brookfield viscometer in an 80:20 mixture of toluene/ethanol.

Examples of suitable hydroxypropylcellulose polymers include KLUCEL® HF Pharm, MF Pharm, GF Pharm JF Pharm, LF Pharm, EF Pharm, and ELF Pharm polymers, available from Ashland.

Examples of suitable hydroxypropylmethylcellulose polymers include PHARIVIACOAT® 603, 645, 606 and 615 polymers, available from Shin-Etsu Chemical Co.

A matrix polymer can comprise, for example, from 90 wt % to 100 wt % of a water-soluble polymer, from 0 wt % to 10 wt %, from 1 wt % to 8 wt %, or from 2 wt % to 6 wt % of a water-soluble polymer, where wt % is based on the total weight of the matrix polymer. A matrix polymer can comprise, for example, greater than 0 wt % of a water-soluble polymer, greater than 2 wt %, greater than 4 wt %, greater than 6 wt %, or greater than 8 wt % of a water-soluble polymer, where wt % is based on the total weight of the matrix polymer. A matrix polymer can comprise, for example, less than 10 wt % of a water-soluble polymer, less than 8 wt %, less than 6 wt %, less than 4 wt %, or less than 2 wt % of a water-soluble polymer, where wt % is based on the total weight of the matrix polymer, where wt % is based on the total weight of the matrix polymer.

A matrix polymer can comprise, for example, from 90 wt % to 100 wt % of a water-insoluble polymer and from 0 wt % to 10 wt % of a water-soluble polymer, from 92 wt % to 98 wt % of a water-insoluble polymer and from 2 wt % to 8 wt % of a water-soluble polymer, or from 94 wt % to 96 wt % of a water-insoluble polymer and from 4 wt % to 6 wt % of a water-soluble polymer, where wt % is based on the total weight of the matrix polymer.

A functional coating can be applied to granules provided by the present disclosure by any suitable method such as by spraying a solution, suspension, or dispersion of the functional coating onto granules in a fluidized bed apparatus.

In addition to a matrix polymer or combination of matrix polymers, a functional coating can comprise, for example, a plasticizing agent, an anti-static, an anti-tacking agent, a colorant or pigment, a glidant, a viscosity modifier, or a combination of any of the foregoing.

A functional coating can comprise an antistatic agent or combination of antistatic agents.

An antistatic agent is useful to minimize or prevent agglomeration of the granules during application of the functional coating.

Examples of suitable antistatic agents include talc, magnesium stearate, and silicon dioxide.

A functional coating can comprise, for example, from 10 wt % to 20 wt % of an antistatic agent, such as from 12 wt % to 18 wt %, or from 14 wt % to 16 wt % of an antistatic agent, where wt % is based on the total weight of the functional coating. A functional coating can comprise, for example, less than 20 wt % of an antistatic agent, less than 18 wt %, less than 16 wt %, less than 14 wt % or less than 12 wt % of an antistatic agent, where wt % is based on the total weight of the functional coating. A functional coating can comprise, for example, greater than 10 wt % of an antistatic agent, greater than 12 wt %, greater than 14 wt %, greater than 16 wt %, or greater than 18 wt % of an antistatic agent, where wt % is based on the total weight of the functional coating.

A functional coating can comprise a plasticizer or combination of plasticizers.

A plasticizer is useful to provide a functional coating having a uniform thickness.

Examples of suitable plasticizers include dibutyl sebacate, polyethylene glycol, triacetin, and triethyl citrate.

A functional coating can comprise, for example, from 0 wt % to 14 wt % of a plasticizer, such as from 2 wt % to 12 wt %, or from 4 wt % to 10 wt % of a plasticizer, where wt % is based on the total weight of the functional coating. A functional coating can comprise, for example, less than 14 wt % of a plasticizer, less than 12 wt %, less than 12 wt %, less than 8 wt %, less than 6 wt %, or less than 4 wt % of a plasticizer, where wt % is based on the total weight of the functional coating. A functional coating can comprise, for example, greater than 0 wt % of a plasticizer, greater than 2 wt %, greater than 4 wt %, greater than 6 wt %, greater than 8 wt %, greater than 10 wt %, or greater than 12 wt % of a plasticizer, where wt % is based on the total weight of the functional coating.

A functional coating provided by the present disclosure can comprise, for example, from 60 wt % to 85 wt % of a matrix polymer, from 10 wt % to 20 wt % of an antistatic agent, and from 0 wt % to 14 wt % of a plasticizer, where wt % is based on the total weight of the functional coating.

A functional coating provided by the present disclosure can comprise, for example, from 65 wt % to 80 wt % of a matrix polymer, from 12 wt % to 18 wt % of an antistatic agent, and from 2 wt % to 12 wt % of a plasticizer, where wt % is based on the total weight of the functional coating.

A functional coating provided by the present disclosure can comprise, for example, from 70 wt % to 80 wt % of a matrix polymer, from 14 wt % to 16 wt % of an antistatic agent, and from 4 wt % to 10 wt % of a plasticizer, where wt % is based on the total weight of the functional coating.

In a functional coating the matrix polymer can comprise ethylcellulose and hydroxypropylcellulose, the plasticizer can comprise dibutyl sebacate, and the antistatic agent can comprise talc.

In a functional coating the matrix polymer can comprise ethylcellulose and hydroxypropylcellulose, the antistatic agent can comprise magnesium stearate, and there can be no plasticizer.

A coated granulation provided by the present disclosure can comprise a seal coat overlying a granule comprising the pharmaceutically active ingredient. A functional coating can overly a seal coat.

The seal coat can minimize the ingress of moisture into the pharmaceutically active ingredient and thereby increase the storage stability of the coated granulation by reducing hydrolysis of the pharmaceutically active ingredient. A seal coat can also minimize negative interactions between the functional coating and the pharmaceutically active ingredient, and thereby increase the storage stability of the coated granulation by reducing hydrolysis of the pharmaceutically active ingredient.

A seal coat can comprise a water-soluble polymer such as, for example, hydroxypropylcellulose, polyvinyl alcohol, hydroxypropylmethylcellulose, hydroxypropylethylcellulose, polyvinylpyrrolidone, or polyethyleneglycol.

A seal coat can have an average thickness, for example, from 0.5 μm to 5 μm, from 1 μm to 4 μm, or from 1 μm to 3 μm. A seal coat can have an average thickness, for example, less than 5 μm, less than 4 μm, less than 3 μm, less than 2 μm, or less than 1 μm.

A seal coat can be applied to a granulation such that the % wg is less than 15% wg, less than 10% wg, less than 8% wg, less than 6% wg, or less than 4% wg. A seal coat can be applied to a granulation such that the % wg is from 1% wg to 15% wg, from 1% wg to 10% wg, from 2% wg to 8% wg, or from 4% wg to 6% wg.

In a coated granulation comprising a seal coating comprising a water-soluble polymer, the functional coating does not contain a water-soluble polymer.

A controlled release granulation provided by the present disclosure can be configured to provide for once a night dosing, once a day dosing (QD), twice a day dosing (BID), three times a day dosing (TID), or four times a day dosing (QID). For example, a controlled release granulation can release substantially 100% of the pharmaceutically active ingredient over a 12-hour duration, an 8-hour duration, or a 4-hour duration.

A controlled release granulation can exhibit a dissolution profile in which less than 80% of the pharmaceutically active ingredient is released from the controlled release granulation within 2 hours, less than 70%, less than 60%, less than 50% or less than 40% is of pharmaceutically active ingredient is released from the controlled release granulation within 2 hours, and greater than 80% or greater than 90% of the pharmaceutically active ingredient is released from the controlled release granulation within 6 hours as determined using a USP Type 2 dissolution apparatus in a buffered solution at pH 4.5 at a temperature of 37° C. and a paddle speed of 75 rpm.

A controlled release granulation can exhibit a dissolution profile in which from 35% to 80%, such as from 40% to 75%, or from 45% to 70% of the pharmaceutically active ingredient is released from the controlled release granulation within 2 hours as determined using a USP Type 2 dissolution apparatus in a buffered solution at pH 4.5 at a temperature of 37° C. and a paddle speed of 75 rpm.

A controlled release granulation can exhibit a dissolution profile in which from 70% to 90%, such as from 75% to 85% of the pharmaceutically active ingredient is released from the controlled release granulation within 4 hours as determined using a USP Type 2 dissolution apparatus in a buffered solution at pH 4.5 at a temperature of 37° C. and a paddle speed of 75 rpm.

A controlled release granulation can exhibit a dissolution profile in which from 80% to 100%, such as from 85% to 95%, of the pharmaceutically active ingredient is released from the controlled release granulation within 6 hours as determined using a USP Type 2 dissolution apparatus in a buffered solution at pH 4.5 at a temperature of 37° C. and a paddle speed of 75 rpm.

A controlled release granulation can exhibit a dissolution profile in which from 35% to 80% of the pharmaceutically active ingredient is released from the controlled release granulation within 2 hours, from 70% to 90% of the pharmaceutically active ingredient is released from the controlled release granulation within 4 hours, and from 80% to 100% of the pharmaceutically active ingredient is released from the formulation within 6 hours, as determined using a USP Type 2 dissolution apparatus in a buffered solution at pH 4.5 at a temperature of 37° C. and a paddle speed of 75 rpm.

A controlled release granulation can exhibit a dissolution profile in which from 45% to 70% of the pharmaceutically active ingredient is released from the controlled release granulation within 2 hours, from 75% to 85% of the pharmaceutically active ingredient is released from the controlled release granulation within 4 hours, and from 85% to 95% of the pharmaceutically active ingredient is released from the controlled release granulation within 6 hours, as determined using a USP Type 2 dissolution apparatus in a buffered solution at pH 4.5 at a temperature of 37° C. and a paddle speed of 75 rpm.

A coated granulation provided by the present disclosure can have a water content, for example, less than 2 wt %, less than 1.5 wt % less than 1 wt %, less than 0.5 wt % or less than 0.25 wt %, where wt % is based on the total weight of the granulation.

A coated granulation provided by the present disclosure can have a water content, for example, from 0.1 wt % to 2 wt %, from 0.1 wt % to 1 wt %, or from 0.2 wt % to 0.5 wt %, where wt % is based on the total weight of the granulation.

A coated pharmaceutical granulation can have a bulk density, for example, greater than 0.55 g/mL, greater than 0.60 g/mL, greater than 0.65 g/mL, greater than 0.70 g/mL, or greater than 0.75 g/mL.

A coated pharmaceutical granulation can have a bulk density, for example, from 0.55 g/mL to 0.80 g/mL, from 0.60 g/mL to 75 g/mL, from 0.60 g/mL to 0.70 g/mL.

Bulk density can be determined using a bulk density cylinder.

A coated pharmaceutical granulation provided by the present disclosure can be characterized, for example, by a PSD (D50), for example, from 150 μm to 350 μm, such as from 175 μm to 325 μm, from 200 μm to 300 μm, or from 225 μm to 275 μm.

A coated pharmaceutical granulation can be characterized, for example, by a PSD (D10) from 50 μm to 150 μm, from 60 μm to 140 μm, from 70 μm, to 120 μm, or from 80 μm to 110 μm.

A coated pharmaceutical granulation can be characterized, for example, by a PSD (D90) from 450 μm to 750 μm, from 475 μm to 725 μm, from 500 μm to 700 μm, from 525 μm to 675 μm, or from 550 μm to 650 μm.

A coated pharmaceutical granulation can be characterized, for example, by a PSD (D10) from 50 μm to 150 μm such as from 60 μm to 140 μm; a PSD (D50) from 230 μm to 310 μm; and a PSD (D90) from 490 μm to 550 μm.

A coated pharmaceutical granulation can be characterized, for example, by a PSD (D10) from 70 μm to 130 μm; a PSD (D50) from 240 μm to 300 μm; and a PSD (D90) from 500 μm to 540 μm.

Figure 15:
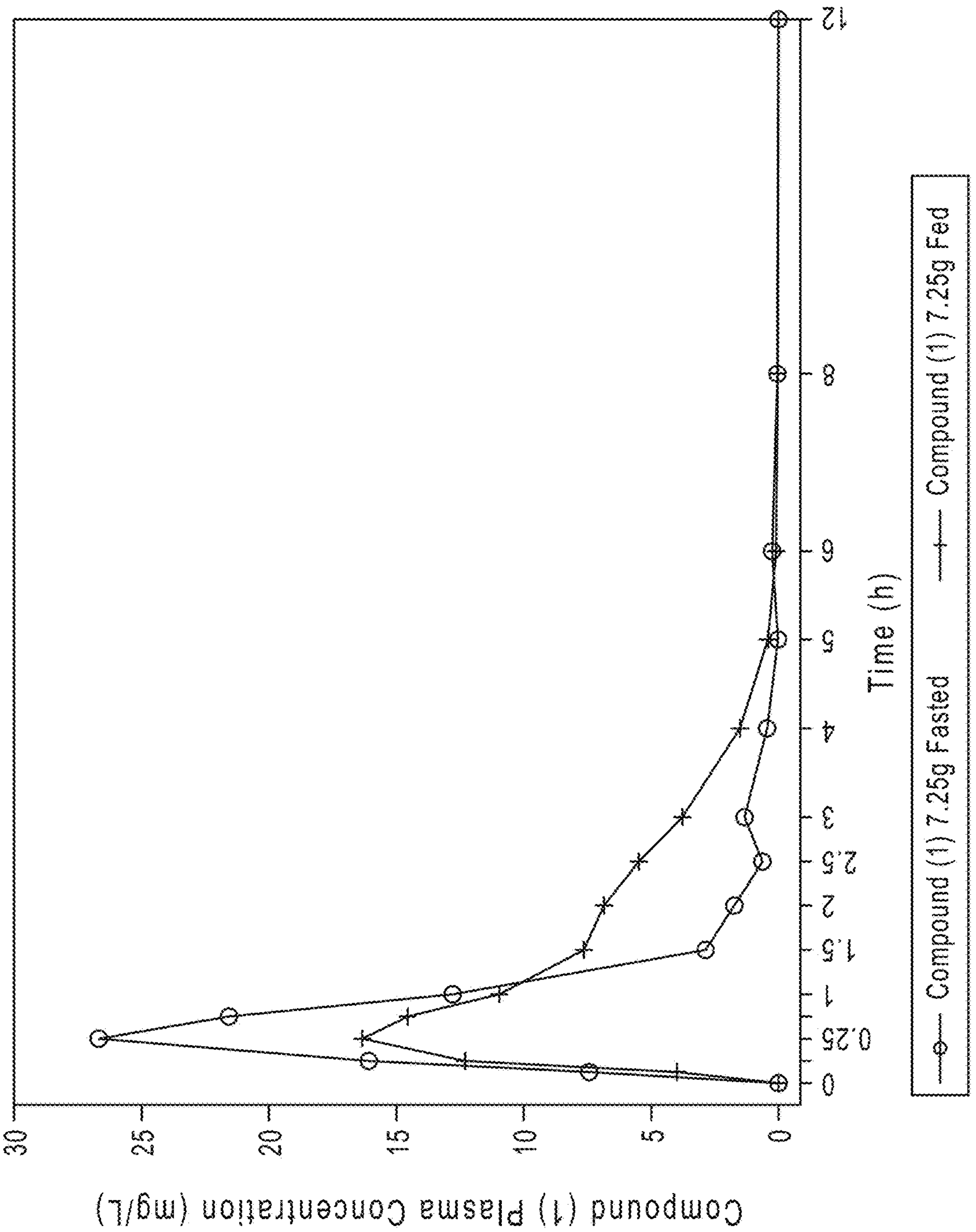
FIG. 15 shows the mean Compound (1) concentration following oral administration of 7.25 g Compound (1) to fasted and to fed healthy subjects.

An example of a PSD for an uncoated granulation provided by the present disclosure is shown in FIG. 15.

A particle size distribution can be determined by laser diffraction or by sieve analysis.

Pharmaceutical compositions provided by the present disclosure can comprise granulations comprising coated granules comprising 4-((L-valyl)oxy)butanoic acid (1).

A pharmaceutical composition can comprise a plurality of coated granules comprising 4-((L-valyl)oxy)butanoic acid (1) suspended in a pharmaceutically acceptable oral solution.

For determination of the pharmacokinetic profiles the pharmaceutical granulations comprised an oral solution of Compound (1) as described in Example 1.

The methods for determining the pharmacokinetic profile for GHB and 4-((L-valyl)oxy)butanoic acid (1) following administration of 4-((L-valyl)oxy)butanoic acid (1) to healthy fasted or fed subjects is provided in the experimental examples.

Following oral administration of an aqueous solution of 7.25 g 4-((L-valyl)oxy)butanoic acid (1) to a population of healthy fasted subjects the plasma GHB concentration profile is characterized by:

a mean $T_{1/2}$ from 0.5 hours to 1.0 hours;
a median $T_{max}$ from 0.75 hours to 1.25 hours;
a mean $C_{max}$ from 90 μg/mL to 150 μg/mL; and
a mean $AUC_{0-inf}$ from 200 h×μg/mL to 500 h×μg/mL.

Following oral administration of an aqueous solution of 7.25 g 4-((L-valyl)oxy)butanoic acid (1) to a population of healthy fasted subjects the plasma GHB concentration profile is characterized by:

a mean $T_{1/2}$ from 0.6 hours to 0.9 hours;
a median $T_{max}$ from 0.8 hours to 1.2 hours;
a mean $C_{max}$ from 100 μg/mL to 140 μg/mL; and
a mean $AUC_{0-inf}$ from 250 h×μg/mL to 450 h×μg/mL.

Following oral administration of an aqueous solution of 7.25 g 4-((L-valyl)oxy)butanoic acid (1) to a population of healthy fasted subjects the plasma GHB concentration profile is characterized by:

a mean $T_{1/2}$ from 0.65 hours to 0.85 hours;
a median $T_{max}$ from 0.9 hours to 1.1 hours;
a mean $C_{max}$ from 110 μg/mL to 130 μg/mL; and
a mean $AUC_{0-inf}$ from 300 h×μg/mL to 400 h×μg/mL.

Following oral administration of an aqueous solution of 7.25 g 4-((L-valyl)oxy)butanoic acid (1) to a population of healthy fasted subjects the plasma GHB concentration profile is characterized by:

a mean $T_{1/2}$ of 0.77 hours;
a median $T_{max}$ of 1.00 hours;
a mean $C_{max}$ of 122 μg/mL; and
a mean $AUC_{0-inf}$ of 353 h×μg/mL.

Following oral administration of an aqueous solution of 7.25 g 4-((L-valyl)oxy)butanoic acid (1) to a population of healthy fed subjects the plasma GHB concentration profile is characterized by:

a mean $T_{1/2}$ from 0.5 hours to 1.1 hours;
a median $T_{max}$ from 1.25 hours to 2.25 hours;
a mean $C_{max}$ from 50 μg/mL to 100 μg/mL; and
a mean $AUC_{0-inf}$ from 130 h×μg/mL to 430 h×μg/mL.

Following oral administration of an aqueous solution of 7.25 g 4-((L-valyl)oxy)butanoic acid (1) to a population of healthy fed subjects the plasma GHB concentration profile is characterized by:

a mean $T_{1/2}$ from 0.6 to 1.0 hours;
a median $T_{max}$ from 1.5 hours to 2.0 hours;
a mean $C_{max}$ from 60 μg/mL to 90 μg/mL; and
a mean $AUC_{0-inf}$ from 180 h×μg/mL to 380 h×μg/mL.

Following oral administration of an aqueous solution of 7.25 g 4-((L-valyl)oxy)butanoic acid (1) to a population of healthy fed subjects the plasma GHB concentration profile is characterized by:

a mean $T_{1/2}$ from 0.7 hours to 0.9 hours;
a median $T_{max}$ from 1.6 hours to 1.9 hours;
a mean $C_{max}$ from 70 μg/mL to 80 μg/mL; and
a mean $AUC_{0-inf}$ from 230 h×μg/mL to 330 h×μg/mL.

Following oral administration of an aqueous solution of 7.25 g 4-((L-valyl)oxy)butanoic acid (1) to a population of healthy fed subjects the plasma GHB concentration profile is characterized by:

a mean $T_{1/2}$ of 0.81 hours;
a median $T_{max}$ of 1.75 hours;
a mean $C_{max}$ of 76 μg/mL; and
a mean $AUC_{0-inf}$ of 382 h×μg/mL.

Following oral administration of an aqueous solution of 7.25 g 4-((L-valyl)oxy)butanoic acid (1) to a population of healthy fasted subjects provides a plasma 4-((L-valyl)oxy)butanoic acid (1) concentration profile characterized by:

a mean $T_{1/2}$ from 0.35 hours to 0.75 hours;
a median $T_{max}$ from 0.5 hours to 1.00 hours;
a mean $C_{max}$ from 17 μg/mL to 37 μg/mL; and
a mean $AUC_{0-inf}$ from 15 h×μg/mL to 30 h×μg/mL.

Following oral administration of an aqueous solution of 7.25 g 4-((L-valyl)oxy)butanoic acid (1) to a population of healthy fasted subjects provides a plasma 4-((L-valyl)oxy)butanoic acid (1) concentration profile characterized by:

a mean $T_{1/2}$ from 0.4 hours to 0.7 hours;
a median $T_{max}$ from 0.6 hours to 0.9 hours;
a mean $C_{max}$ from 20 μg/mL to 34 μg/mL; and
a mean $AUC_{0-inf}$ from 17 h×μg/mL to 28 h×μg/mL.

Following oral administration of an aqueous solution of 7.25 g 4-((L-valyl)oxy)butanoic acid (1) to a population of healthy subjects patient provides a plasma 4-((L-valyl)oxy)butanoic acid (1) concentration profile characterized by:

a mean $T_{1/2}$ from 0.45 hours to 0.65 hours;
a median $T_{max}$ from 0.65 hours to 0.85 hours;
a mean $C_{max}$ from 23 μg/mL to 31 μg/mL; and
a mean $AUC_{0-inf}$ from 19 h×μg/mL to 29 h×μg/mL.

Following oral administration of an aqueous solution of 7.25 g 4-((L-valyl)oxy)butanoic acid (1) to a population of healthy fasted subjects provides a plasma 4-((L-valyl)oxy)butanoic acid (1) concentration profile characterized by:

a mean $T_{1/2}$ of 0.54 hours;
a median $T_{max}$ of 0.75 hours;
a mean $C_{max}$ of 27.7 μg/mL; and
a mean $AUC_{0-inf}$ of 22.4 h×μg/mL.

Following oral administration of an aqueous solution of 7.25 g 4-((L-valyl)oxy)butanoic acid (1) to a population of healthy fed subjects provides a plasma 4-((L-valyl)oxy)butanoic acid (1) concentration profile characterized by:

a mean $T_{1/2}$ from 0.35 hours to 0.95 hours;
a median $T_{max}$ from 0.25 hours to 0.75 hours;
a mean $C_{max}$ from 11 μg/mL to 25 μg/mL; and
a mean $AUC_{0-inf}$ from 21 h×μg/mL to 37 h×μg/mL.

Following oral administration of an aqueous solution of 7.25 g 4-((L-valyl)oxy)butanoic acid (1) to a population of healthy fed subjects provides a plasma 4-((L-valyl)oxy) butanoic acid (1) concentration profile characterized by:

a mean $T_{1/2}$ from 0.45 hours to 0.85 hours;

a median $T_{max}$ from 0.35 hours to 0.65 hours;

a mean $C_{max}$ from 14 μg/mL to 22 μg/mL; and a mean $AUC_{0\text{-}inf}$ from 23 h×μg/mL to 35 h×μg/mL.

Following oral administration of an aqueous solution of 7.25 g 4-((L-valyl)oxy)butanoic acid (1) to a population of healthy fed subjects provides a plasma 4-((L-valyl)oxy) butanoic acid (1) concentration profile characterized by:

a mean $T_{1/2}$ from 0.55 hours to 0.75 hours;

a median $T_{max}$ from 0.45 hours to 0.55 hours;

a mean $C_{max}$ from 16 μg/mL to 20 μg/mL; and a mean $AUC_{0\text{-}inf}$ from 26 h×μg/mL to 32 h×μg/mL.

Following oral administration of an aqueous solution of 7.25 g expression "4-((L-valyl)oxy)butanoic acid (1)" with the expression "4-((L-valyl)oxy)butanoic acid (Compound 1)". to a population of healthy fed subjects provides a plasma expression "4-((L-valyl)oxy)butanoic acid (1)" with the expression "4-((L-valyl)oxy)butanoic acid (Compound 1)". concentration profile characterized by:

a mean $T_{1/2}$ of 0.64 hours;

a median $T_{max}$ of 0.5 hours;

a mean $C_{max}$ of 18.1 μg/mL; and a mean $AUC_{0\text{-}inf}$ of 29.0 h×μg/mL.

Figure 16:
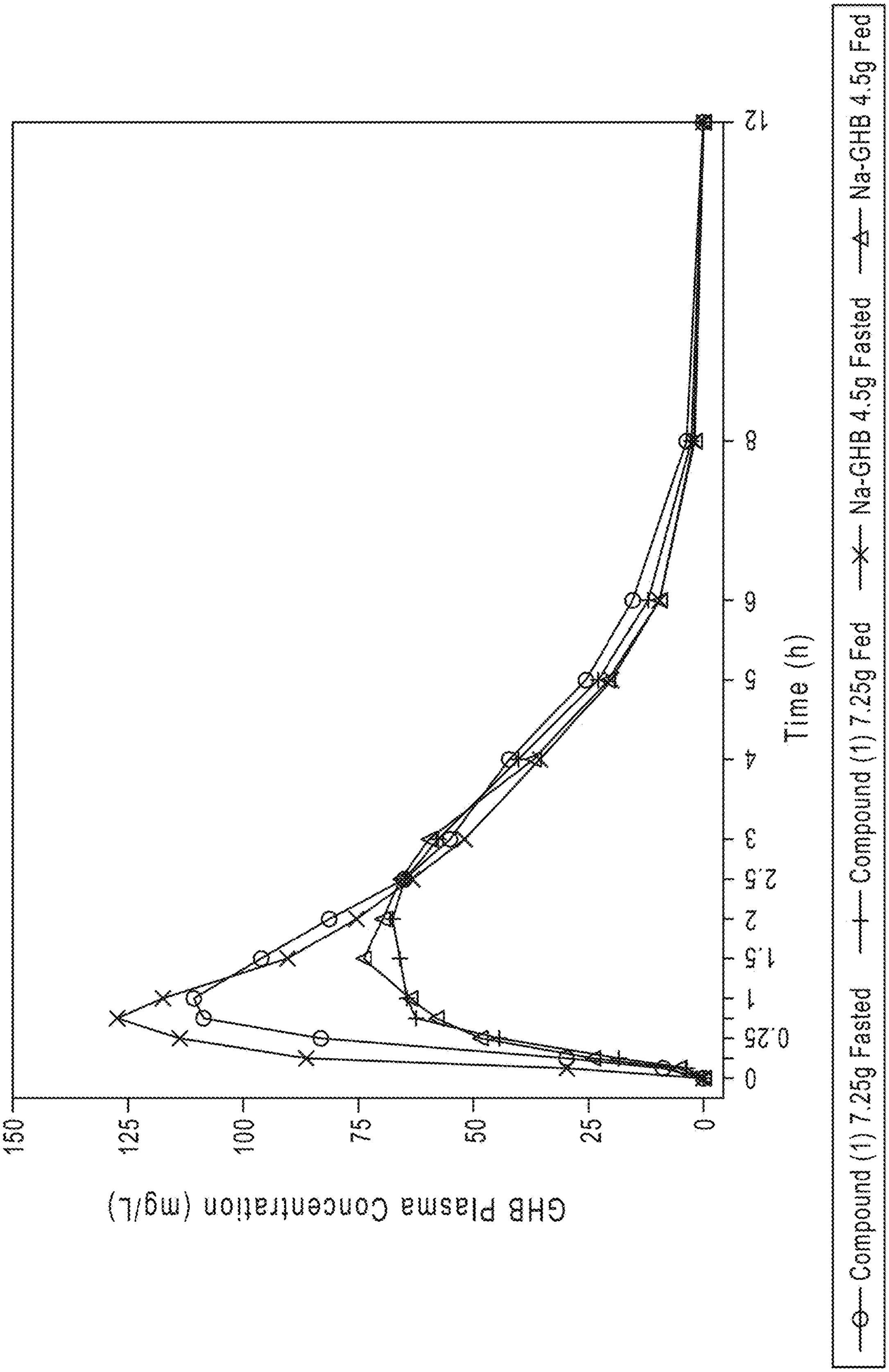
FIG. 16 shows the mean γ-hydroxybutyric acid plasma concentration following oral administration of 7.25 g of Compound (1) or 4.5 g of sodium oxybate to fasted and to fed healthy subjects.

Following oral administration of an aqueous solution of 4-((L-valyl)oxy)butanoic acid (1) to a population of healthy fasted or fed subjects a GHB plasma concentration profile characterized by the parameters disclosed in any of Tables 8, 14-16, and 19 and the pharmacokinetic profiles shown in FIG. 16.

Following oral administration of an aqueous solution of 4-((L-valyl)oxy)butanoic acid (1) to a population of healthy fasted or fed subjects a 4-((L-valyl)oxy)butanoic acid (1) plasma concentration profile characterized by the parameters disclosed in any of Tables 7, 10-12, and 18 and the pharmacokinetic profiles shown in FIG. 15.

Pharmaceutical compositions provided by the present disclosure include pharmaceutical compositions that when orally administered provide a GHB plasma concentration that is bioequivalent to any of the pharmacokinetic profiles disclosed herein including, for example, a pharmacokinetic profile characterized by the parameters disclosed in Tables 8, 14-16, and 19 and the pharmacokinetic profiles shown in FIG. 16.

Pharmaceutical compositions provided by the present disclosure include pharmaceutical compositions that when orally administered provide a 4-((L-valyl)oxy)butanoic acid (1) plasma concentration that is bioequivalent to any of the pharmacokinetic profiles disclosed herein including, for example, a pharmacokinetic profile characterized by the parameters disclosed in Tables 7, 10-12, and 18 and the pharmacokinetic profiles shown in FIG. 15

Pharmaceutical compositions provided by the present disclosure include pharmaceutical compositions that when orally administered provide a $C_{max}$ and/or AUC of the GHB plasma concentration that is bioequivalent to the plasma GHB $C_{max}$ and/or AUC of any of the pharmacokinetic profiles disclosed herein including, for example, a pharmacokinetic profile characterized by the parameters disclosed in Tables 8, 14-16, and 19 and the pharmacokinetic profiles shown in FIG. 16.

Pharmaceutical compositions provided by the present disclosure include pharmaceutical compositions that when orally administered provide a $C_{max}$ and/or AUC of the 4-((L-valyl)oxy)butanoic acid (1) plasma concentration that is bioequivalent to the plasma GHB $C_{max}$ and/or AUC of any of the pharmacokinetic profiles disclosed herein including, for example, a pharmacokinetic profile characterized by the parameters disclosed in Tables 8, 14-16, and 19 and the pharmacokinetic profiles shown in FIG. 16.

The pharmaceutical compositions can comprise an aqueous solution of 4-((L-valyl)oxy)butanoic acid (1) at a dose of from 0.1 g to 20 g 4-((L-valyl)oxy)butanoic acid (1).

The pharmaceutical compositions can comprise an aqueous solution comprising a dose of from 0.1 g-equivalents to 10 g-equivalents GHB.

γ-Hydroxybutyric acid and the γ-hydroxybutyric acid derivative of Formula (1) (Compound 1)) can be used to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, and fibromyalgia γ-Hydroxybutyric acid and the γ-hydroxybutyric acid derivative of Formula (1) (Compound (1)) can be used to treat rapid eye movement ("REM") sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, and anxiety.

ASPECTS OF THE INVENTION

The invention is further defined by the following aspects.

Aspect 1. A pharmaceutical composition comprising a plurality of coated granules, wherein the plurality of coated granules comprises 4-((L-valyl)oxy)butanoic acid (1) or a pharmaceutically acceptable salt thereof:

(1)

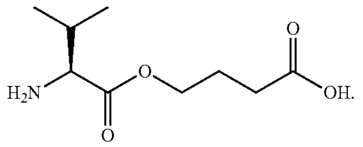

Aspect 2. The pharmaceutical composition of aspect 1, wherein the plurality of coated granules comprises from 60 wt % to 85 wt % of 4-((L-valyl)oxy)butanoic acid (1), wherein wt % is based on the total weight of the plurality of granules.

Aspect 3. The pharmaceutical composition of any one of aspects 1 to 2, wherein coated granules comprise a core and a functional coating surrounding the core, wherein, the core comprises greater than 90 wt % of 4-((L-valyl)oxy)butanoic acid (1), wherein wt % is based on the total weight of the core; and the plurality of coated granules has an average particle size distribution (PSD) (D50) from 150 μm to 400 μm, wherein PSD is determined by sieve analysis.

Aspect 4. The pharmaceutical composition of aspect 3, wherein the functional coating comprises a controlled release coating.

Aspect 5. The pharmaceutical composition of any one of aspects 3 to 4, wherein the functional coating comprises: from 60 wt % to 85 wt % of a matrix polymer; from 10 wt % to 20 wt % of an antistatic agent; and from 0 wt % to 14 wt % of a plasticizer, wherein wt % is based on the total weight of the functional coating.

Aspect 6. The pharmaceutical composition of any one of aspects 3 to 5, wherein, the core represents from 65 wt % to 85 wt % of the total weight of the plurality of coated granules; and the functional coating represents from 15 wt % to 35 wt % of the total weight of the plurality of coated granules.

Aspect 7. The pharmaceutical composition of any one of aspects 3 to 6, wherein the functional coating has a thickness from 5 μm to 20 μm.

Aspect 8. The pharmaceutical composition of any one of aspects 1 to 7, wherein the plurality of coated granules has a water content less than 1 wt %, wherein wt % is based on the total weight of the plurality of coated granules.

Aspect 9. The pharmaceutical composition of any one of aspects 1 to 8, wherein the pharmaceutical composition comprises a pharmaceutically acceptable oral suspension of the plurality of coated granules.

Aspect 10. The pharmaceutical composition of any one of aspects 1 to 9, wherein the pharmaceutical composition comprises from 0.1 grams to 20 grams of 4-((L-valyl)oxy) butanoic acid (1).

Aspect 11. The pharmaceutical composition of any one of aspects 1 to 10, wherein following oral administration of an aqueous solution comprising 7.25 g of 4-((L-valyl)oxy) butanoic acid (1) to a population of fasted subjects the plasma GHB concentration profile is characterized by: a mean $T_{1/2}$ from 0.5 hours to 1.0 hours; a median $T_{max}$ from 0.75 hours to 1.25 hours; a mean $C_{max}$ from 90 μg/mL to 150 μg/mL; and a mean $AUC_{0-inf}$ from 200 h×μg/mL to 500 h×μg/mL.

Aspect 12. The pharmaceutical composition of any one of aspects 1 to 11, wherein following oral administration of an aqueous solution comprising 7.25 g of 4-((L-valyl)oxy) butanoic acid (1) to a population of fed subjects the plasma GHB concentration profile is characterized by: a mean $T_{1/2}$ from 0.5 hours to 1.1 hours; a median $T_{max}$ from 1.25 hours to 2.25 hours; a mean $C_{max}$ from 50 μg/mL to 100 μg/mL; and a mean $AUC_{0-inf}$ from 130 h×μg/mL to 430 h×μg/mL.

Aspect 13. The pharmaceutical composition of any one of aspects 1 to 12, wherein following oral administration of an aqueous solution comprising 7.25 g of 4-((L-valyl)oxy) butanoic acid (1) to a population of fasted subjects the plasma 4-((L-valyl)oxy)butanoic acid (1) concentration profile characterized by: a mean $T_{1/2}$ from 0.35 hours to 0.75 hours; a median $T_{max}$ from 0.5 hours to 1.00 hours; a mean $C_{max}$ from 17 μg/mL to 37 μg/mL; and a mean $AUC_{0-inf}$ from 15 h×μg/mL to 30 h×μg/mL.

Aspect 14. The pharmaceutical composition of any one of aspects 1 to 13, wherein following oral administration of an aqueous solution comprising 7.25 g of 4-((L-valyl)oxy) butanoic acid (1) to a population of fed patient the plasma 4-((L-valyl)oxy)butanoic acid (1) concentration profile characterized by: a mean $T_{1/2}$ from 0.35 hours to 0.95 hours; a median $T_{max}$ from 0.25 hours to 0.75 hours; a mean $C_{max}$ from 11 μg/mL to 25 μg/mL; and a mean $AUC_{0-inf}$ from 21 h×μg/mL to 37 h×μg/mL.

Aspect 15. A method of treating fatigue or excessive daytime sleepiness associated with narcolepsy comprising orally administering to a patient in need thereof the pharmaceutical composition of any one of aspects 1 to 14.

Aspect 16. The method of aspect 15, wherein administering comprises administering QD.

Aspect 17. The method of aspect 15, wherein administering comprises administering BID.

Aspect 18. A method of treating narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia comprising orally administering to a patient in need thereof the pharmaceutical composition of any one of aspects 1 to 14.

Aspect 19. A method of treating a symptom associated with narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia comprising orally administering to a patient in need thereof the pharmaceutical composition of any one of aspects 1 to 14.

Aspect 20. A method of treating REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety comprising orally administering to a patient in need thereof the pharmaceutical composition of any one of aspects 1 to 14.

Aspect 21. A method of treating a symptom associated with REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety comprising orally administering to a patient in need thereof the pharmaceutical composition of any one of aspects 1 to 14.

Aspect 1A A pharmaceutical composition comprising an aqueous solution comprising 4-((L-valyl)oxy)butanoic acid (1) or a pharmaceutically acceptable salt thereof.

Aspect 2A. The pharmaceutical composition of aspect 1A, wherein the pharmaceutical concentration comprises a concentration of 4-((L-valyl)oxy)butanoic acid (1) from 80 mg/mL to 120 mg/mL.

Aspect 3A. The pharmaceutical composition of any one of aspects 1A to 2A, wherein the pharmaceutical composition comprises from 2.7 gm-equivalents to 4.7 gm-equivalents of γ-hydroxybutyric acid.

Aspect 4A. The pharmaceutical composition of any one of aspects 1A to 3A, wherein the pharmaceutical composition comprises from 6.5 g to 8.5 g of 4-((L-valyl)oxy)butanoic acid (1).

Aspect 5A. The pharmaceutical composition of any one of aspects 1A to 4A, wherein the pharmaceutical composition has a pH from 4.0 to 5.0.

Aspect 6A. The pharmaceutical composition of any one of aspects 1A to 5A, wherein the 4-((L-valyl)oxy)butanoic acid (1) is stable within 98% of the initial amount for 96 hours at 25° C.

Aspect 7A. The pharmaceutical composition of any one of aspects 1A to 6A, wherein following oral administration of the pharmaceutical composition comprising 7.5 g of 4-((L-valyl)oxy)butanoic acid (1) to a population of fasted subjects the plasma pharmacokinetic profile of γ-hydroxybutyric acid is characterized by: a mean $T_{1/2}$ from 0.7 hours to 0.9 hours; a median $T_{max}$ from 0.8 hours to 1.2 hours; a mean $C_{max}$ from 102 μg/mL to 132 μg/mL; and a mean $AUC_{0-inf}$ from 333 h×μg/mL to 373 h×μg/mL.

Aspect 8A. The pharmaceutical composition of any one of aspects 1A to 6A, wherein following oral administration of the pharmaceutical composition comprising 7.5 μm of 4-((L-valyl)oxy)butanoic acid (1) to a population of fed subjects the plasma pharmacokinetic profile of γ-hydroxybutyric acid is characterized by: a mean $T_{1/2}$ from 0.7 hours to 0.9 hours; a median $T_{max}$ from 1.6 hours to 2.0 hours; a mean $C_{max}$ from 135 μg/mL to 155 μg/mL; and a mean $AUC_{0-inf}$ from 330 h×μg/mL to 370 h×μg/mL.

Aspect 9A. The pharmaceutical composition of any one of aspects 1A to 6A, wherein following oral administration the composition provides a γ-hydroxybutyric acid plasma concentration that is bioequivalent to the plasma concentration versus time cure shown in FIG. 16.

Aspect 10A. The pharmaceutical composition of any one of aspects 1A to 6A, wherein following oral administration the composition provides a γ-hydroxybutyric acid plasma concentration that is bioequivalent to the plasma concentration versus time cure of any of the pharmacokinetic profiles described in Tables 14, 15, 16, and 19.

Aspect 11A. The pharmaceutical composition of any one of aspects 1A to 10A, wherein the pharmaceutical composition comprises: from 82 wt % to 92 wt % of 4-((L-valyl) oxy)butanoic acid (1); from 5 wt % to 9 wt % of a pH adjusting agent; from 3 wt % to 7 wt % of a sweetening agent; and from 0.2 wt % to 0.6 wt % of a flavoring agent; wherein, wt % is based on the total solids weight of the pharmaceutical composition; the pharmaceutical composition is an aqueous composition; and the pharmaceutical composition has a pH from 4.0 to 5.0.

Aspect 12A. The pharmaceutical composition of any one of aspects 1A to 10A, wherein the pharmaceutical composition comprises: from 82 wt % to 92 wt % of 4-((L-valyl) oxy)butanoic acid (1); from 5 wt % to 9 wt % malic acid; from 3 wt % to 7 wt % sucralose; and from 0.2 wt % to 0.6 wt % of a flavoring agent; wherein, wt % is based on the total solids weight of the pharmaceutical composition; and the pharmaceutical composition is an aqueous composition.

Aspect 13A. The pharmaceutical composition of any one of aspects 1A to 10A, wherein the pharmaceutical composition comprises: from 84 wt % to 90 wt % of 4-((L-valyl) oxy)butanoic acid (1); from 6 wt % to 8 wt % malic acid; from 4 wt % to 6 wt % sucralose; and from 0.3 wt % to 0.5 wt % flavoring; wherein wt % is based on the total solids weight of the pharmaceutical composition.

Aspect 14A. The pharmaceutical composition of any one of aspects 1A to 13A, wherein the pharmaceutical composition comprises a modified release component.

Aspect 15A. The pharmaceutical composition of aspect 14A, wherein the modified release component comprises coated granules comprising 4-((L-valyl)oxy)butanoic acid (1).

Aspect 16A. The pharmaceutical composition of aspect 15A, wherein the coated granules comprise a functional coating.

Aspect 17A. The pharmaceutical composition of any one of aspects 15A and 16A, wherein the coated granules are suspended in the aqueous solution.

Aspect 18A. A pharmaceutical composition, comprising: an immediate release component, wherein the immediate release component comprises the pharmaceutical composition of any one of aspects 1A to 13A; and a modified release component, wherein the modified release component comprise coated granules comprising 4-((L-valyl)oxy)butanoic acid.

Aspect 19A. A method of providing a therapeutically effective amount of γ-hydroxybutyric acid in the plasma of a patient comprising orally administering to a patient in need thereof the pharmaceutical composition of any one of aspects 1A to 18A.

Aspect 20A. The method of aspect 19A, wherein the subject is fasted.

Aspect 21A. The method of aspect 19A, wherein the subject is fed.

Aspect 22A. The method of aspect 19A, wherein the dose of is from 2.7 gm-equivalents to 4.7 gm-equivalents γ-hydroxybutyric acid.

Aspect 23A. A method of treating a disease in a patient in need thereof comprising orally administering the pharmaceutical composition of any one of aspects 1A to 18A to the patient.

Aspect 24A. The method of aspect 23A, wherein administering comprises administering once per day.

Aspect 25A. The method of aspect 23A, wherein administering comprises administering twice per day.

Aspect 26A. The method of any one of aspects 23A to 25A, wherein the disease is fatigue or excessive daytime sleepiness associated with narcolepsy.

Aspect 27A. The method of any one of aspects 23A to 25A, wherein the disease is narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia.

Aspect 28. The method of any one of aspects 23A to 25A, wherein the disease is REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety.

Aspect 29A. A method of providing a plasma pharmacokinetic profile of γ-hydroxybutyric acid in a subject that is bioequivalent to a plasma pharmacokinetic profile of γ-hydroxybutyric acid following oral administration of sodium oxybate, comprising administering an equivalent dose of γ-hydroxybutyric acid in the form of 4-((L-valyl)oxy)butanoic acid (1).

EXAMPLES

Embodiments provided by the present disclosure are further illustrated by reference to the following examples, which describe the pharmacokinetics of Compound (1) and GHB following oral administration to fasted or fed healthy subjects. It will be apparent to those skilled in the art that many modifications, both to materials, and methods, may be practiced without departing from the scope of the disclosure. It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

General Description

The plasma concentrations of Compound (1) and GHB in plasma in healthy human subjects were measured using liquid chromatography tandem mass-spectroscopy and evaluated using the non-compartmental analysis software program PHOENIX™ WINNONLIN® version 8.1 (Pharsight Corporation, USA) and the spreadsheet software program MICROSOFT® EXCEL® (Microsoft Corporation, USA).

All randomized subjects who received Compound (1), with available pharmacokinetic (PK) data and without relevant deviations interfering with the PK evaluations, were included. Subjects who received only placebo were excluded from the PK population. In addition, the PK population was used for the summaries and analyses of all PK data.

Example 1

Oral Formulation

An aqueous oral solution of Compound (1) included the constituents listed in Table 1.

TABLE 1

Aqueous oral solution of Compound (1).

| Ingredient | mg/mL | Function | Specification |
|---|---|---|---|
| Compound (1) | 100 | Active Ingredient | Enterprise Standard |
| Malic Acid | 8 | pH Regulator | USP/NF |
| Sucralose | 6 | Sweetening Agent | USP/NF |
| Essence (Strawberry) | 0.5 | Flavoring Agent | USP/NF |
| Purified Water | 1 | Solvent | Enterprise Standard |

To prepare the aqueous oral solution, Compound (1), provided as a white to off-white solid, was dissolved in purified water using a magnetic stir bar and the solution filtered. Malic acid, sucralose, and strawberry essence were added to the filtered solution, with the volume brought up with purified water. A nominal concentration was 100 mg/mL.

The aqueous oral solution was stable for at least 96 hours (98% of initial) at 25° C. and at from 2° C. to 8° C. The chiral purity under the same conditions was 99.5% for at least 96 hours.

The aqueous oral solution was used administered to healthy subjects as described in the following examples.

The 24 h stability results of Compound (1) in different pH solution indicated that the stability increased with pH decreasing. Based on these stability results, malic acid was selected as to adjust the pH. The results of the stability testing are shown in Table 2.

TABLE 2

Stability of Compound (1) at ddifferent pH.

| pH | Purity (Area %) initial | 5 hours | 24 hours |
|---|---|---|---|
| Water | 99.14 | 98.75 | 97.17 |
| pH 1.2 | 99.25 | 99.22 | 98.95 |
| pH 4.5 | 99.25 | 99.05 | 98.35 |
| pH 6.8 | 99.08 | 97.58 | 93.14 |
| pH 7.4 | 98.84 | 95.74 | 87.89 |

Based on the stability results of Compound (1) in different pH solution malic acid and citric acid were initially selected to adjust solution pH value to 4.5. Formulation 1 and Formulation 2 were prepared to evaluate the stability of Compound (1) using either malic acid or citric acid to adjust the pH at 25° C. The constituents of the two formulations are presented in Table 3.

TABLE 3

Formulations used to screen pH adjusting agents.

| | Formulation 1 | | Formulation 2 | |
|---|---|---|---|---|
| Materials | mg/mL | g/50 mL | mg/mL | g/50 mL |
| Compound (1) | 100 | 5.0 | 100 | 5.0 |
| Malic Acid | adjust pH | 1.211 | N/A | N/A |
| Citric Acid | N/A | N/A | adjust pH | 1.173 |
| Purified Water | about 1 | about 50 | about 1 | about 50 |

TABLE 4

Stability of Compound (1) at pH 4.5 and 25° C. in the presence of different acids.

| | Individual impurities (%) | | Total impurities | Avg. assay | Chiral purity |
|---|---|---|---|---|---|
| | L-valine 48 h | [1] RRT = 1.21 48 h | (%) 48 h | (%) 0 d | (%) 48 h |
| Formulation 1 | 0.71 | 0.04 | 0.7 | 96.1 | 99.6 |
| Formulation 2 | 0.83 | 0.04 | 0.9 | 93.5 | 99.6 |

[1] Relative Retention Time ("RRT").

Based on the results presented in Table 4, malic acid was selected as the pH adjusting agent. The effect of the amount of malic acid on the stability of Compound (1) was then evaluated using the formulations described in Table 5.

TABLE 5

Formulations used to screen for the amount of malic acid.

| | Formulation 3 | | Formulation 4 | | Formulation 4 | |
|---|---|---|---|---|---|---|
| Ingredient | mg/mL | g/50 mL | mg/mL | g/50 mL | mg/mL | g/50 mL |
| Compound (1) | 100 | 5.0 | 100 | 5.0 | 100 | 5.0 |
| Malic Acid | 8 | 0.4 | 6 | 0.3 | 4 | 0.2 |
| Purified Water | about 1 | about 50 | about 1 | about 50 | about 1 | about 50 |

The results are presented in Table 6.

TABLE 6

Solution sstability with different amounts of a pH adjusting agent at room ttemperature.

| | Individual impurities (%) | | | | | | | |
|---|---|---|---|---|---|---|---|---|
| | L-valine | | RRT = 1.21 | | Total impurities (%) | | Avg. assay (%) | |
| | 0 d | 48 h | 0 d | 48 h | 0 d | 48 h | 0 d | 48 h |
| Formulation 3 | 0.29 | 0.80 | 0.05 | 0.05 | 0.3 | 0.9 | 102.0 | 99.5 |
| Formulation 4 | 0.30 | 0.85 | 0.05 | 0.05 | 0.3 | 0.9 | 100.9 | 98.9 |
| Formulation 4 | 0.30 | 0.88 | 0.05 | 0.06 | 0.4 | 0.9 | 100.6 | 98.4 |

Compared to the other two formulations, there was less increase in impurity L-valine for the Formulation 1 and therefore the amount of malic acid was selected as 8 mg/mL.

Example 2

Single Ascending Dose Study

A randomized, double-blind, single-center, single ascending dose study was undertaken to evaluate the safety, tolerability, and pharmacokinetics of Compound (1) and GHB in healthy subjects.

Compound (1) was administered to randomized healthy subjects at doses from 0.1 g to 7.25 g as an aqueous solution of Compound (1) in water. The subjects fasted for at least 10 hours overnight with clear liquids allowed prior to dosing and the subjects were fasted for 4 hours after dosing.

Plasma samples were obtained at various times following oral administration and the plasma concentrations of Compound (1) and GHB were measured.

Selected pharmacokinetic parameters of Compound (1) following oral administration of different doses of Compound (1) is shown in Table 7.

TABLE 7

Selected PK parameters for Compound (1).

| Cohort (dose) | Subject Identification | $t_{1/2}$ (h) | $T_{max}$ (h) | $C_{max}$ (ng/mL) | $AUC_{0-tlast}$ (h × ng/mL) | $AUC_{0-inf}$ (h × ng/mL) | CL/F (L/h) |
|---|---|---|---|---|---|---|---|
| 1 | N | 4 | 4 | 4 | 4 | 4 | 4 |
| (0.10 g) | Mean | 0.70 | — | 420 | 249 | 250 | 420 |
| | SD | 0.23 | — | 188 | 62 | 63 | 109 |
| | Min | 0.48 | 0.25 | 265 | 180 | 180 | 316 |
| | Median | 0.71 | 0.25 | 373 | 250 | 252 | 408 |
| | Max | 0.92 | 0.25 | 669 | 315 | 316 | 554 |
| 2 | N | 4 | 4 | 4 | 4 | 4 | 4 |
| (0.50 g) | Mean | 1.11 | — | 1543 | 1291 | 1294 | 400 |
| | SD | 0.29 | — | 625 | 275 | 276 | 85 |
| | Min | 0.71 | 0.50 | 1160 | 998 | 1000 | 309 |
| | Median | 1.19 | 0.75 | 1270 | 1277 | 1278 | 396 |
| | Max | 1.33 | 1.50 | 2470 | 1610 | 1620 | 500 |
| 3 | N | 3 | 4 | 4 | 4 | 3 | 3 |
| (1.50 g) | Mean | 1.04 | — | 3365 | 2863 | 2475 | 673 |
| | SD | 0.07 | — | 1496 | 1061 | 876 | 284 |
| | Min | 0.97 | 0.25 | 2100 | 1500 | 1500 | 468 |
| | Median | 1.06 | 1.00 | 2915 | 2957 | 2712 | 553 |
| | Max | 1.11 | 1.50 | 5530 | 4040 | 3210 | 959 |
| 4 | N | 6 | 6 | 6 | 6 | 6 | 6 |
| (3.00 g) | Mean | 1.15 | — | 11290 | 7511 | 7515 | 413 |
| | SD | 0.25 | — | 3405 | 1490 | 1490 | 85 |
| | Min | 0.78 | 0.25 | 7440 | 5500 | 5500 | 318 |
| | Median | 1.12 | 0.50 | 11150 | 7406 | 7410 | 408 |
| | Max | 1.54 | 1.00 | 15200 | 9430 | 9430 | 545 |
| 5 | N | 6 | 6 | 6 | 6 | 6 | 6 |
| (4.50 g) | Mean | 1.14 | — | 12820 | 11140 | 11400 | 416 |
| | SD | 0.25 | — | 3621 | 1860 | 1856 | 87 |

TABLE 7-continued

Selected PK parameters for Compound (1).

| Cohort (dose) | Subject Identification | $t_{1/2}$ (h) | $T_{max}$ (h) | $C_{max}$ (ng/mL) | $AUC_{0-tlast}$ (h × ng/mL) | $AUC_{0-inf}$ (h × ng/mL) | CL/F (L/h) |
|---|---|---|---|---|---|---|---|
| | Min | 0.83 | 0.25 | 6790 | 7660 | 7670 | 353 |
| | Median | 1.13 | 0.75 | 14050 | 11580 | 11590 | 389 |
| | Max | 1.50 | 0.75 | 16700 | 12700 | 12700 | 586 |
| 6 | N | 6 | 6 | 6 | 6 | 6 | 6 |
| (6.00 g) | Mean | 1.18 | — | 17620 | 18350 | 18360 | 340 |
| | SD | 0.32 | — | 3844.7 | 4228 | 4240 | 71 |
| | Min | 0.79 | 0.50 | 13200 | 14200 | 14200 | 232 |
| | Median | 1.18 | 0.50 | 16500 | 17980 | 17980 | 334 |
| | Max | 1.64 | 0.75 | 22900 | 25800 | 25800 | 423 |
| 7 | N | 6 | 6 | 6 | 6 | 6 | 6 |
| (7.25 g) | Mean | 1.11 | — | 22130 | 19550 | 19560 | 376 |
| | SD | 0.17 | — | 3396 | 2689 | 2685 | 47 |
| | Min | 0.92 | 0.50 | 16800 | 16700 | 16700 | 298 |
| | Median | 1.12 | 0.62 | 22150 | 19360 | 19360 | 375 |
| | Max | 1.28 | 0.75 | 26000 | 24300 | 24300 | 433 |

Figure 2:
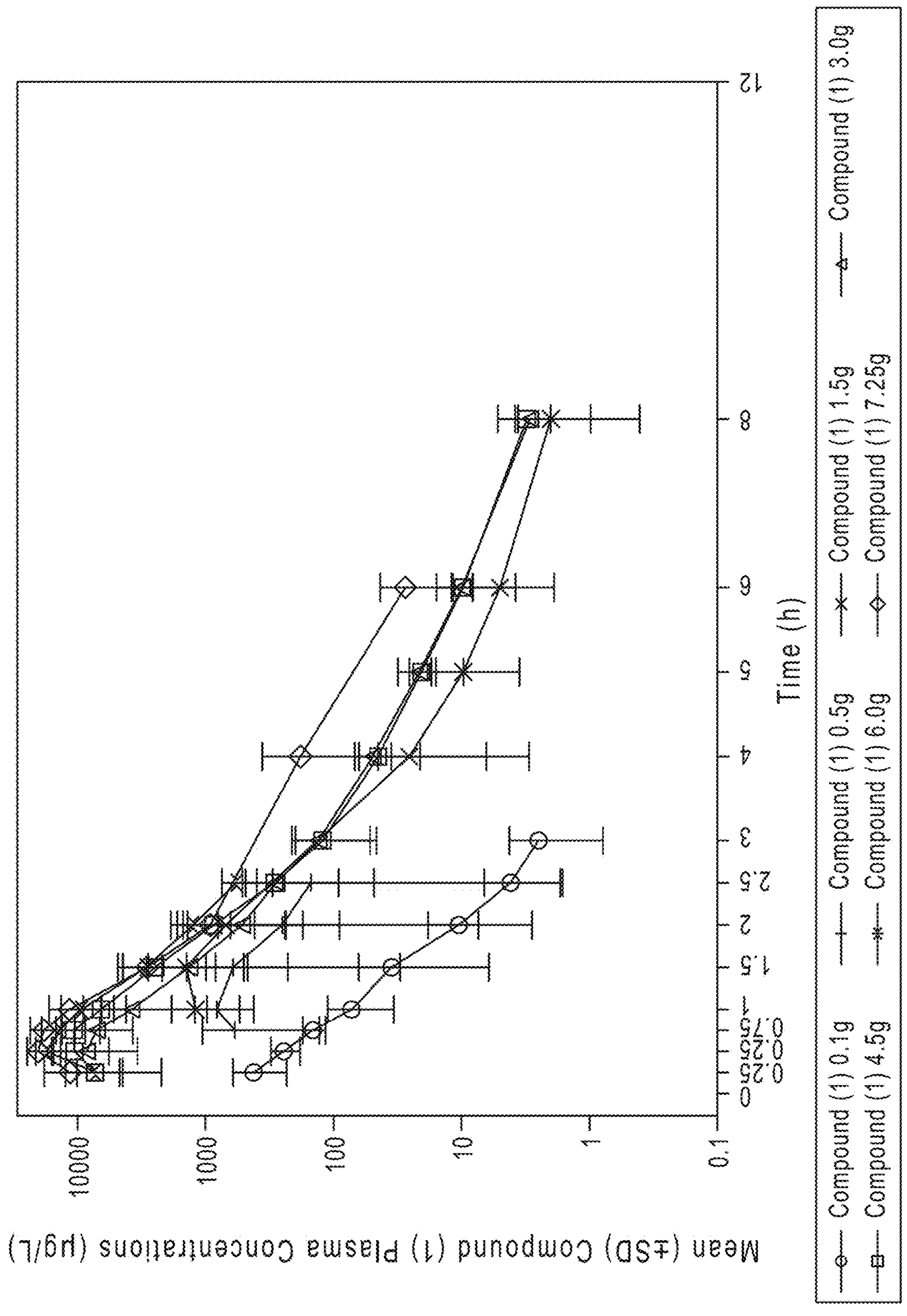
FIG. 2 shows the mean Compound (1) plasma concentration following oral administration of Compound (1) to healthy subjects.

The mean and standard deviation ("SD") of the plasma Compound (1) concentration (mg/L) is shown in FIG. 1 (linear scale) and in FIG. 2 (log-linear scale).

Figure 3:
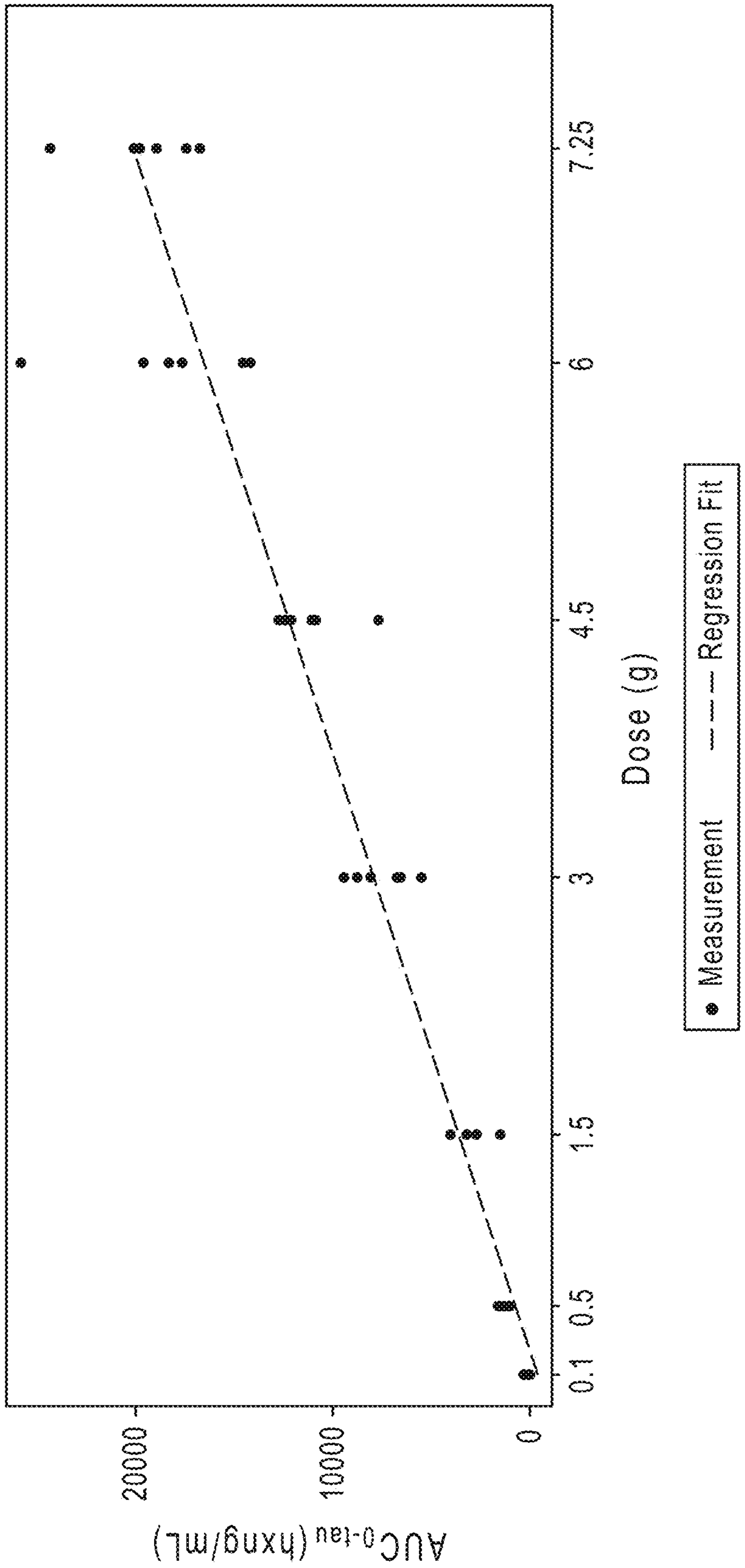
FIG. 3 shows the Compound (1) plasma area under the curve at time tau ("$AUC_{tau}$") following oral administration of different doses of Compound (1) to healthy subjects.

The mean plasma Compound (1) $AUC_{0-inf}$(h×mg/L) with increasing doses of Compound (1) is shown in FIG. 3.

Figure 4:
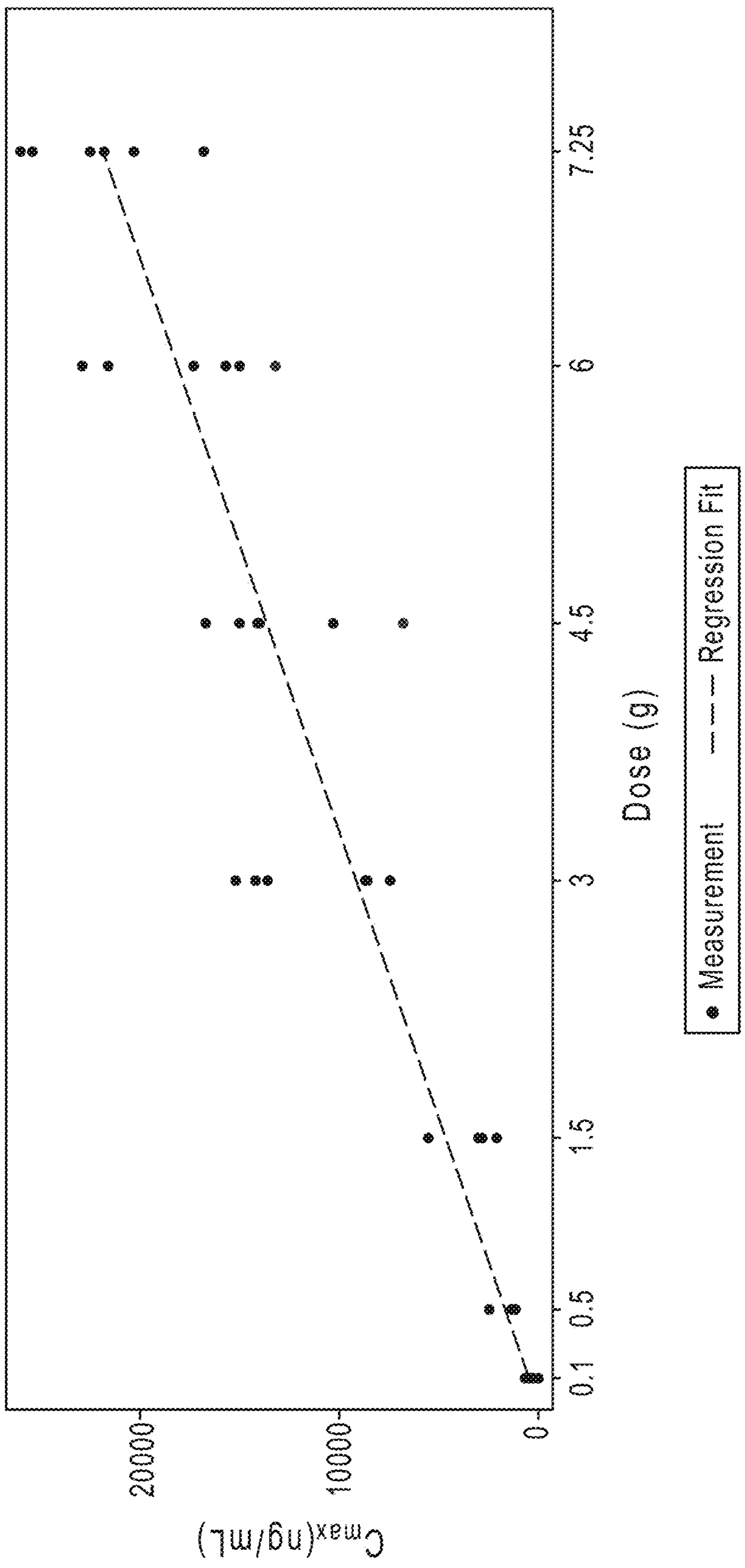
FIG. 4 shows the Compound (1) maximum plasma concentration ("$C_{max}$") following oral administration of different doses of Compound (1) to healthy subjects.

The mean plasma Compound (1) $C_{max}$ (mg/L) with increasing doses of Compound (1) is shown in FIG. 4.

Selected pharmacokinetic parameters of GHB following oral administration of different doses of Compound (1) is shown in Table 8.

TABLE 8

Selected PK parameters for GHB.

| Cohort (dose) | Subject ID | $t_{1/2}$ (h) | $T_{max}$ (h) | $C_{max}$ (mg/L) | $AUC_{0-tlast}$ (h × mg/L) | $AUC_{0-inf}$ (h × mg/L) |
|---|---|---|---|---|---|---|
| 1 | N | 4 | 4 | 4 | 4 | 4 |
| (0.10 g) | Mean | 0.49 | — | 0.7 | 0.51 | 0.56 |
| | SD | 0.12 | — | 0.3 | 0.14 | 0.15 |
| | Min | 0.33 | 0.25 | 0.3 | 0.33 | 0.38 |
| | Median | 0.50 | 0.25 | 0.7 | 0.55 | 0.59 |
| | Max | 0.61 | 0.50 | 0.8 | 0.63 | 0.69 |
| 2 | N | 4 | 4 | 4 | 4 | 4 |
| (0.50 g) | Mean | 0.77 | — | 4.0 | 3.68 | 3.76 |
| | SD | 0.32 | — | 2.2 | 0.92 | 0.92 |
| | Min | 0.32 | 0.50 | 2.0 | 2.9 | 2.95 |
| | Median | 0.84 | 0.88 | 3.4 | 3.4 | 3.51 |
| | Max | 1.07 | 1.50 | 7.0 | 5.0 | 5.07 |
| 3 | N | 3 | 4 | 4 | 4 | 3 |
| (1.50 g) | Mean | 0.99 | — | 15.6 | 20.9 | 15.3 |
| | SD | 0.38 | — | 5.5 | 12.5 | 6.4 |
| | Min | 0.73 | 0.50 | 9.2 | 9.4 | 9.5 |
| | Median | 0.81 | 1.13 | 15.5 | 18.1 | 14.3 |

TABLE 8-continued

Selected PK parameters for GHB.

| Cohort (dose) | Subject ID | $t_{1/2}$ (h) | $T_{max}$ (h) | $C_{max}$ (mg/L) | $AUC_{0\text{-}tlast}$ (h × mg/L) | $AUC_{0\text{-}inf}$ (h × mg/L) |
|---|---|---|---|---|---|---|
| | Max | 1.42 | 2.00 | 22.3 | 38.0 | 22.1 |
| 4 | N | 6 | 6 | 6 | 6 | 6 |
| (3.00 g) | Mean | 1.29 | — | 41.2 | 59.5 | 60 |
| | SD | 0.66 | — | 9.7 | 17.7 | 18 |
| | Min | 0.78 | 0.50 | 30.0 | 43.9 | 44 |
| | Median | 0.97 | 0.75 | 40.3 | 52.4 | 53 |
| | Max | 2.50 | 1.00 | 53.8 | 88.1 | 88 |
| 5 | N | 6 | 6 | 6 | 6 | 6 |
| (4.50 g) | Mean | 0.73 | — | 64.8 | 124.5 | 125 |
| | SD | 0.21 | — | 7.7 | 12.4 | 12 |
| | Min | 0.45 | 0.75 | 55.0 | 108.3 | 108 |
| | Median | 0.70 | 1.00 | 66.2 | 127 | 127 |
| | Max | 1.06 | 1.50 | 76.2 | 139 | 140 |
| 6 | N | 6 | 6 | 6 | 6 | 6 |
| (6.00 g) | Mean | 0.88 | — | 84.5 | 204 | 204 |
| | SD | 0.28 | — | 23.4 | 70 | 70 |
| | Min | 0.65 | 0.75 | 57.3 | 135 | 135 |
| | Median | 0.80 | 1.25 | 82.6 | 185 | 185 |
| | Max | 1.42 | 4.00 | 117.0 | 324 | 324 |
| 7 | N | 6 | 6 | 6 | 6 | 6 |
| (7.25 g) | Mean | 0.79 | — | 91.5 | 238 | 238 |
| | SD | 0.13 | — | 18.2 | 74 | 74 |
| | Min | 0.58 | 0.75 | 74.6 | 142 | 142 |
| | Median | 0.83 | 1.00 | 90.0 | 278 | 279 |
| | Max | 0.96 | 1.50 | 124 | 294 | 295 |

Figure 5:
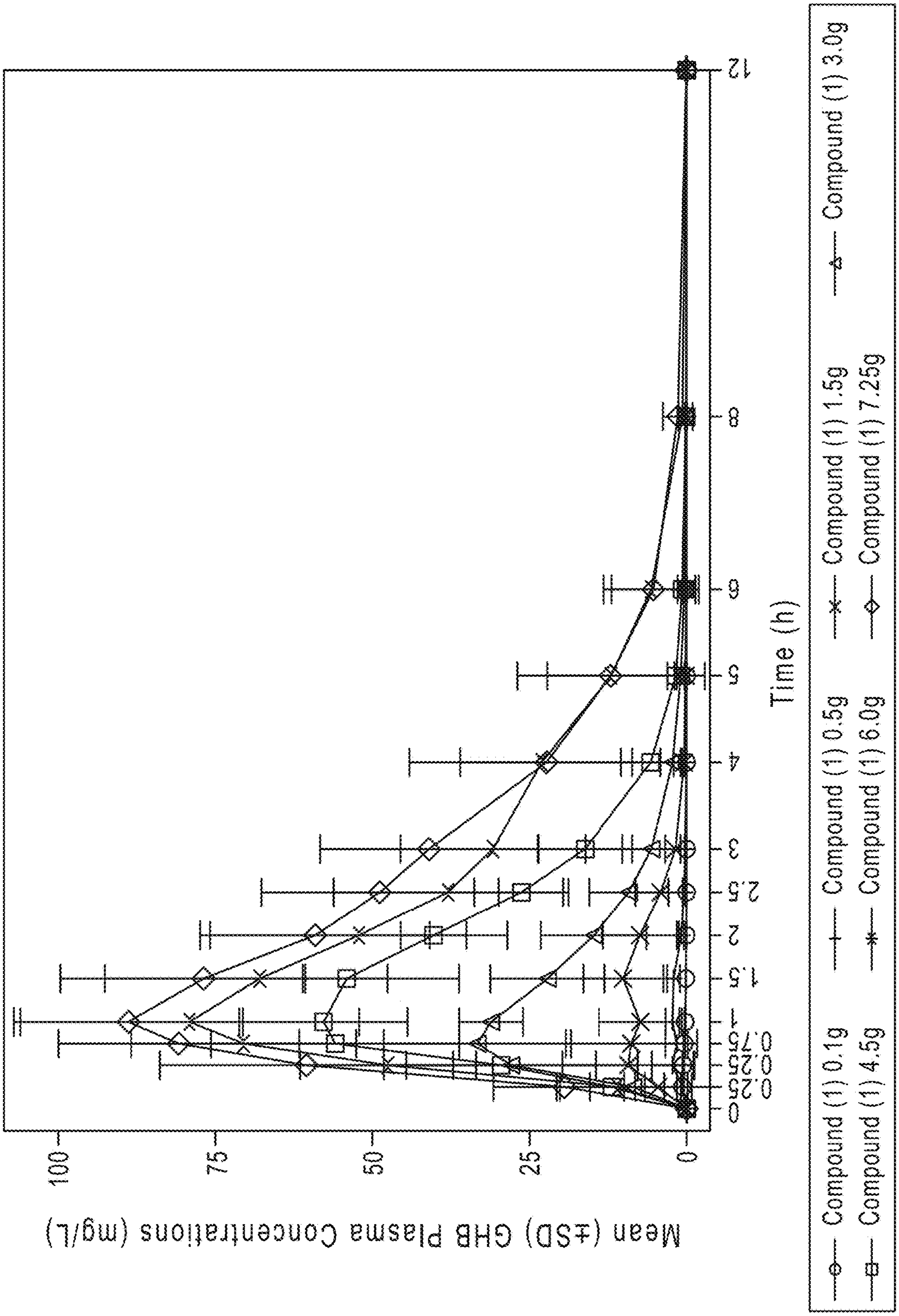
FIG. 5 shows the mean γ-hydroxybutyric acid plasma concentration following oral administration of Compound (1) to healthy subjects.
Figure 6:
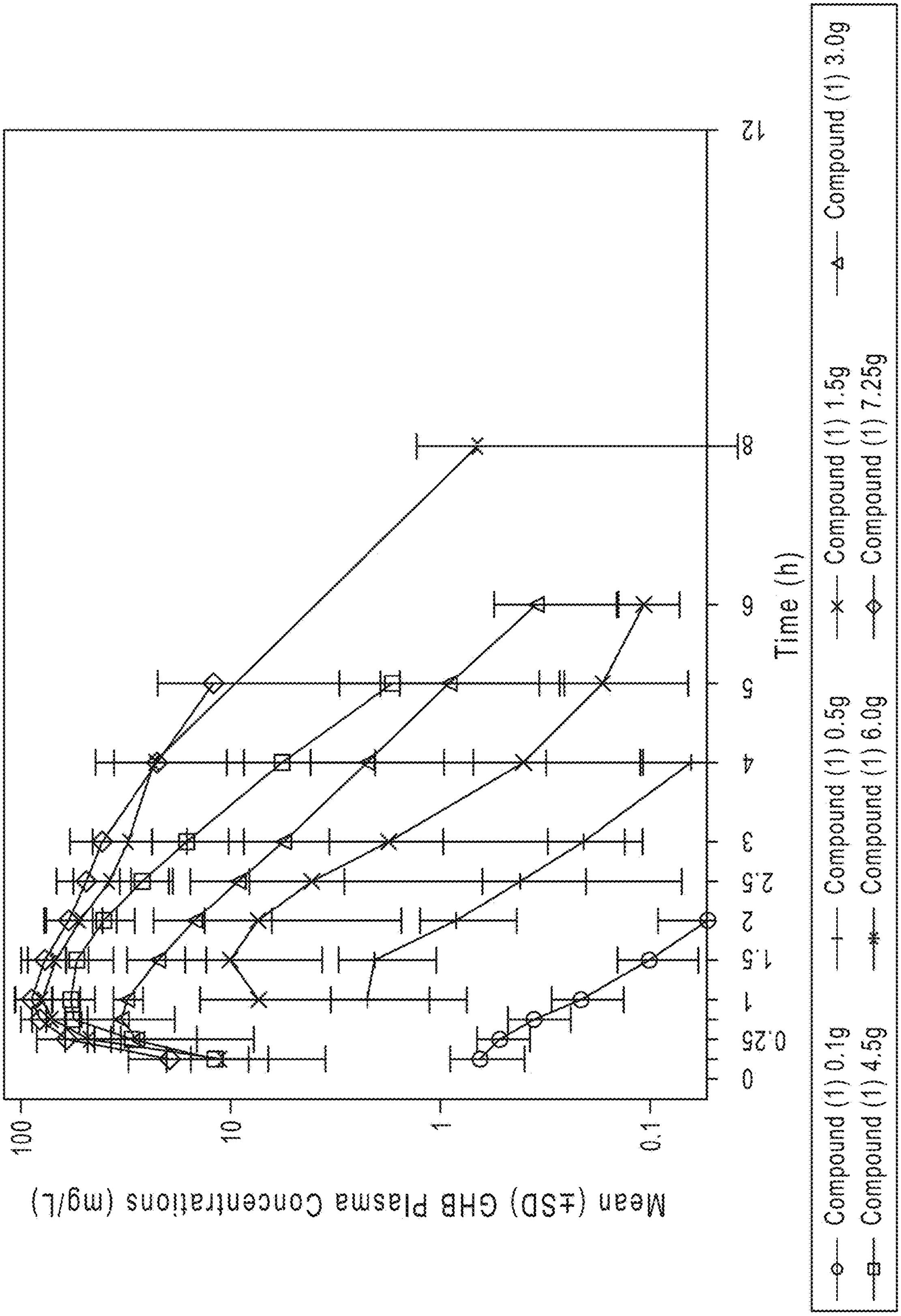
FIG. 6 shows the mean γ-hydroxybutyric acid plasma concentration following oral administration of Compound (1) to healthy subjects.

The mean (SD) plasma GHB concentration (mg/L) is shown in FIG. 5 (linear scale) and in FIG. 6 (log-linear scale).

Figure 7:
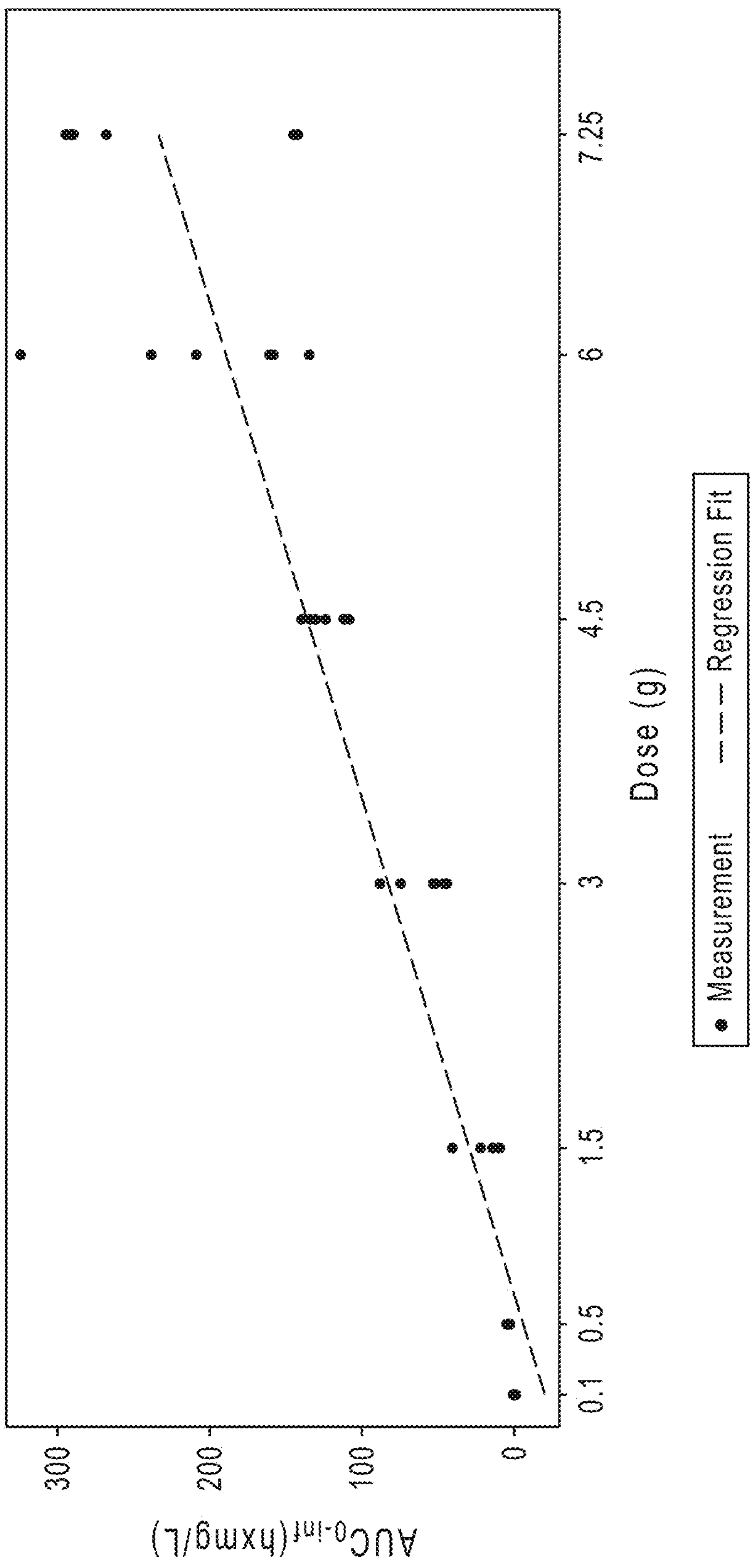
FIG. 7 shows the γ-hydroxybutyric acid plasma area under the cure from time 0 to infinity ("$AUC_{inf}$") following oral administration of different doses of Compound (1) to healthy subjects.

The mean plasma GHB $AUC_{0\text{-}inf}$ (h×mg/L) with increasing doses of Compound (1) is shown in FIG. 7.

Figure 8:
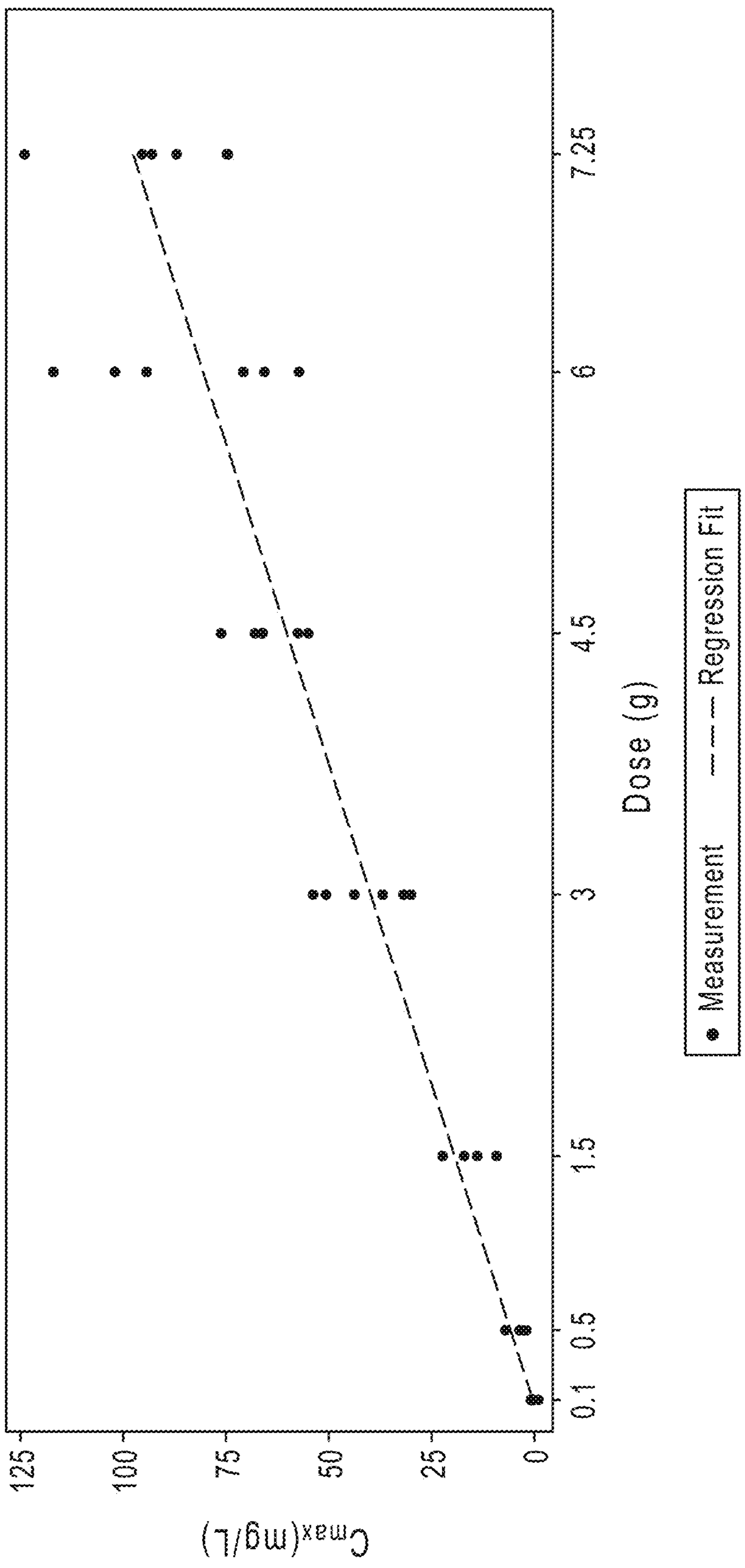
FIG. 8 shows the γ-hydroxybutyric acid plasma $C_{max}$ following oral administration of different doses of Compound (1) to healthy subjects.

The mean plasma GHB $C_{max}$ (mg/L) with increasing doses of Compound (1) is shown in FIG. 8.

Example 3

Multiple Ascending Dose Study

A multiple ascending dose study was undertaken to evaluate the pharmacokinetics of multiple doses of Compound (1) in 3 cohorts of healthy subjects (with 8 subjects/cohort). Within each cohort, the subjects were randomized to receive Compound (1) or placebo at a ratio of 6:2 (active: placebo) for 7 days (or up to 9 days if the cohort included a titration period).

After fasting for at least 3 hours following a standard meal, subjects were randomized on Day 1 and the first dose of study drug (either target dose or titration dose) was administered. The first cohort of subjects (Cohort 8) received the second dose administration at approximately four hours after receiving the first dose. The subsequent 3 cohorts (Cohorts 9 and 10) received only one dose per day. A summary of the dosing for the cohorts is provided in Table 9.

TABLE 9

Oral doses of Compound (1) and matching placebo administered over 7 days.

| Cohort | Dose (g) |
|---|---|
| 8 | 6.0 divided into two equal doses, administered 4 hours apart |
| 9 | 4.5 g single daily dose |
| 10 | 6.0 g single daily dose |

For the first cohort (Cohort 8), the dose used was 6.0 g divided into two equal doses four hours apart for 7 days starting from Day 4 "Dose Day 1" to Day 10 "Dose Day 7". Subsequent Cohorts 9, 10 received a single daily dose of 4.5 g and 6.0 g during the titration period (Day 1 for Cohort 9, Day 1 and Day 2 for Cohort 10, and after a titration period for 7 days starting from Day 4 "Dose Day 1" to Day 10 "Dose Day 7". Cohort 11 was not conducted due to API availability.

Selected pharmacokinetic parameters of Compound (1) for Cohorts 8, 9, and 10 are shown in Tables 10, 11, and 12, respectively.

TABLE 10

Selected PK parameters for plasma Compound (1) concentration for Cohort 8 (6.0 g/day divided into equal 2 doses).

| Dosing Day | Statistic | $T_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) | CL/F (L/h) |
|---|---|---|---|---|---|---|---|
| 4 | N | 6 | 6 | 6 | 6 | 6 | 6 |
| | Mean | 0.53 | — | 12.1 | 14.4 | 14.5 | 431 |
| | SD | 0.66 | — | 2.6 | 3.2 | 3.3 | 105 |
| | Min | 0.22 | 0.25 | 9.6 | 10.0 | 10.1 | 315 |
| | Median | 0.27 | 0.50 | 11.5 | 14.8 | 14.8 | 405 |
| | Max | 1.87 | 4.50 | 16.7 | 19.0 | 19.1 | 597 |
| 10 | N | 6 | 6 | 6 | 6 | 6 | 6 |
| | Mean | 0.34 | — | 11.5 | 14.8 | 14.9 | 430 |
| | SD | 0.11 | — | 2.9 | 4.2 | 4.2 | 114 |
| | Min | 0.24 | 0.50 | 8.7 | 10.5 | 10.7 | 280 |
| | Median | 0.28 | 0.50 | 11.3 | 14.1 | 14.1 | 430 |
| | Max | 0.52 | 4.75 | 17.0 | 21.4 | 21.5 | 569 |

TABLE 11

Selected PK parameters for plasma Compound (1) concentration for Cohort 9 (4.5 g/day in a single dose).

| Dosing Day | Statistic | $T_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) | CL/F (L/h) |
|---|---|---|---|---|---|---|---|
| 4 | N | 5 | 6 | 6 | 6 | 5 | 5 |
| | Mean | 0.49 | — | 15.6 | 11.3 | 12.0 | 378 |
| | SD | 0.17 | — | 2.8 | 1.6 | 0.8 | 25 |
| | Min | 0.28 | 0.25 | 10.5 | 8.3 | 11.1 | 338 |
| | Median | 0.54 | 0.50 | 16.8 | 11.7 | 11.8 | 382 |
| | Max | 0.68 | 0.75 | 17.8 | 13.2 | 13.3 | 406 |
| 10 | N | 6 | 6 | 6 | 6 | 6 | 6 |
| | Mean | 0.56 | — | 14.8 | 10.7 | 10.8 | 423 |
| | SD | 0.18 | — | 3.1 | 1.7 | 1.7 | 59 |
| | Min | 0.37 | 0.50 | 9.3 | 9.1 | 9.2 | 323 |
| | Median | 0.56 | 0.50 | 15.9 | 10.1 | 10.2 | 443 |
| | Max | 0.84 | 0.50 | 17.8 | 13.8 | 13.9 | 488 |

TABLE 12

Selected PK parameters for plasma Compound (1) concentration for Cohort 10 (6.0 g/day in a single dose).

| Dosing Day | Statistic | $T_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) | CL/F (L/h) |
|---|---|---|---|---|---|---|---|
| 4 | N | 6 | 6 | 6 | 6 | 6 | 6 |
| | Mean | 0.41 | — | 21.3 | 17.1 | 17.2 | 390 |
| | SD | 0.07 | — | 6.6 | 5.4 | 5.4 | 163 |
| | Min | 0.34 | 0.33 | 10.5 | 8.7 | 8.8 | 265 |
| | Median | 0.40 | 0.50 | 23.5 | 18.9 | 19.0 | 316 |
| | Max | 0.51 | 0.50 | 28.0 | 22.6 | 22.7 | 684 |
| 10 | N | 5 | 5 | 5 | 5 | 5 | 5 |
| | Mean | 0.36 | — | 18.9 | 16.3 | 16.4 | 395 |
| | SD | 0.09 | — | 4.8 | 4.9 | 4.9 | 128 |
| | Min | 0.29 | 0.50 | 11.7 | 10.4 | 10.4 | 284 |
| | Median | 0.35 | 0.50 | 20.0 | 16.8 | 16.9 | 354 |
| | Max | 0.52 | 0.75 | 24.5 | 21.1 | 21.1 | 575 |

Figure 9:
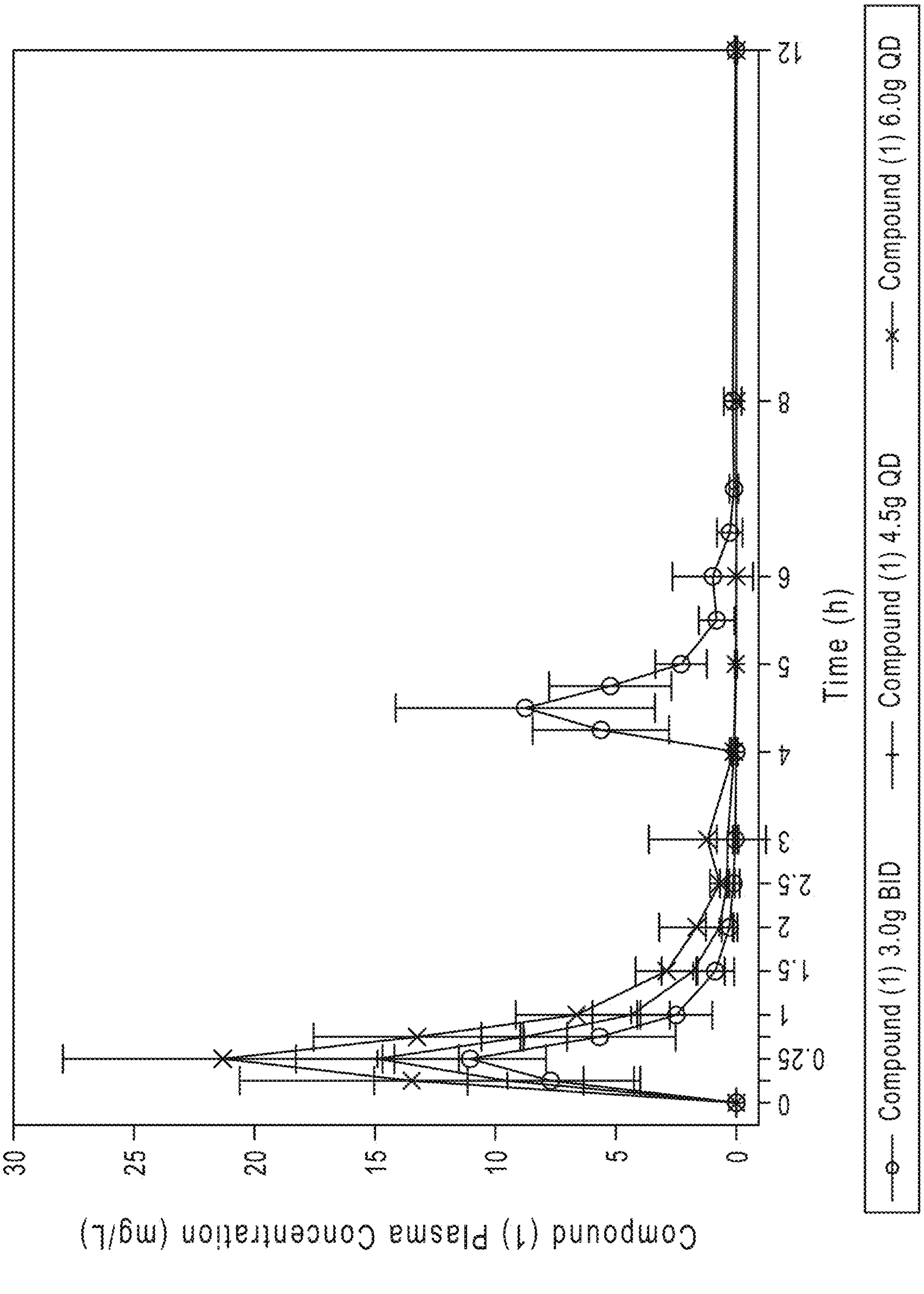
FIG. 9 shows the mean γ-hydroxybutyric acid plasma $AUC_{tau}$ following oral administration of different doses and dosing regimens of Compound (1) to healthy subjects.
Figure 10:
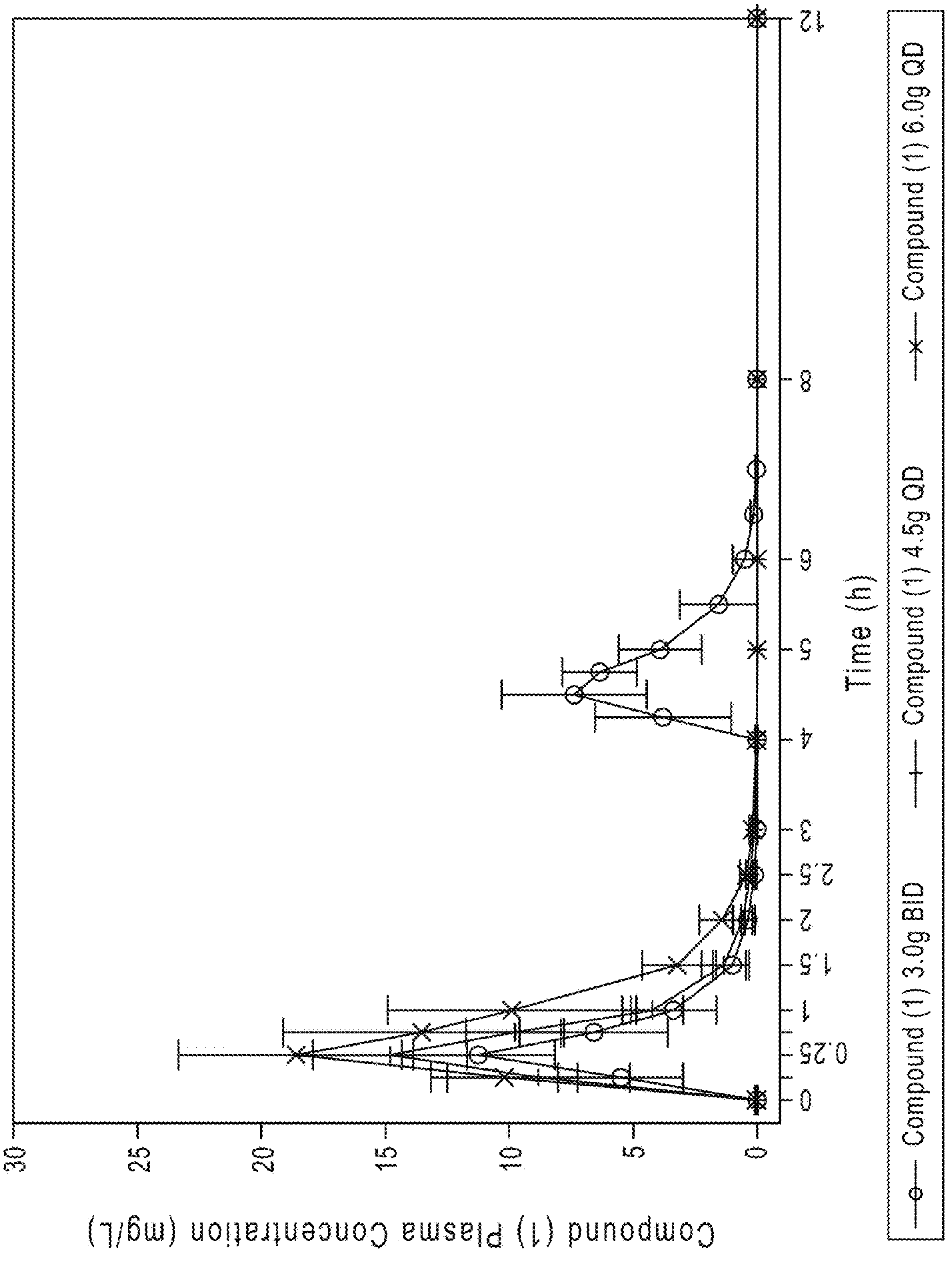
FIG. 10 shows the mean γ-hydroxybutyric acid plasma $C_{max}$ following oral administration of different doses and dosing regimens of Compound (1) to healthy subjects.

Pharmacokinetic profiles of the mean plasma Compound (1) concentration (mg/L) for the three cohorts are shown in FIGS. 9 and 10 at Day 4 and at Day 10, respectively.

Figure 11:
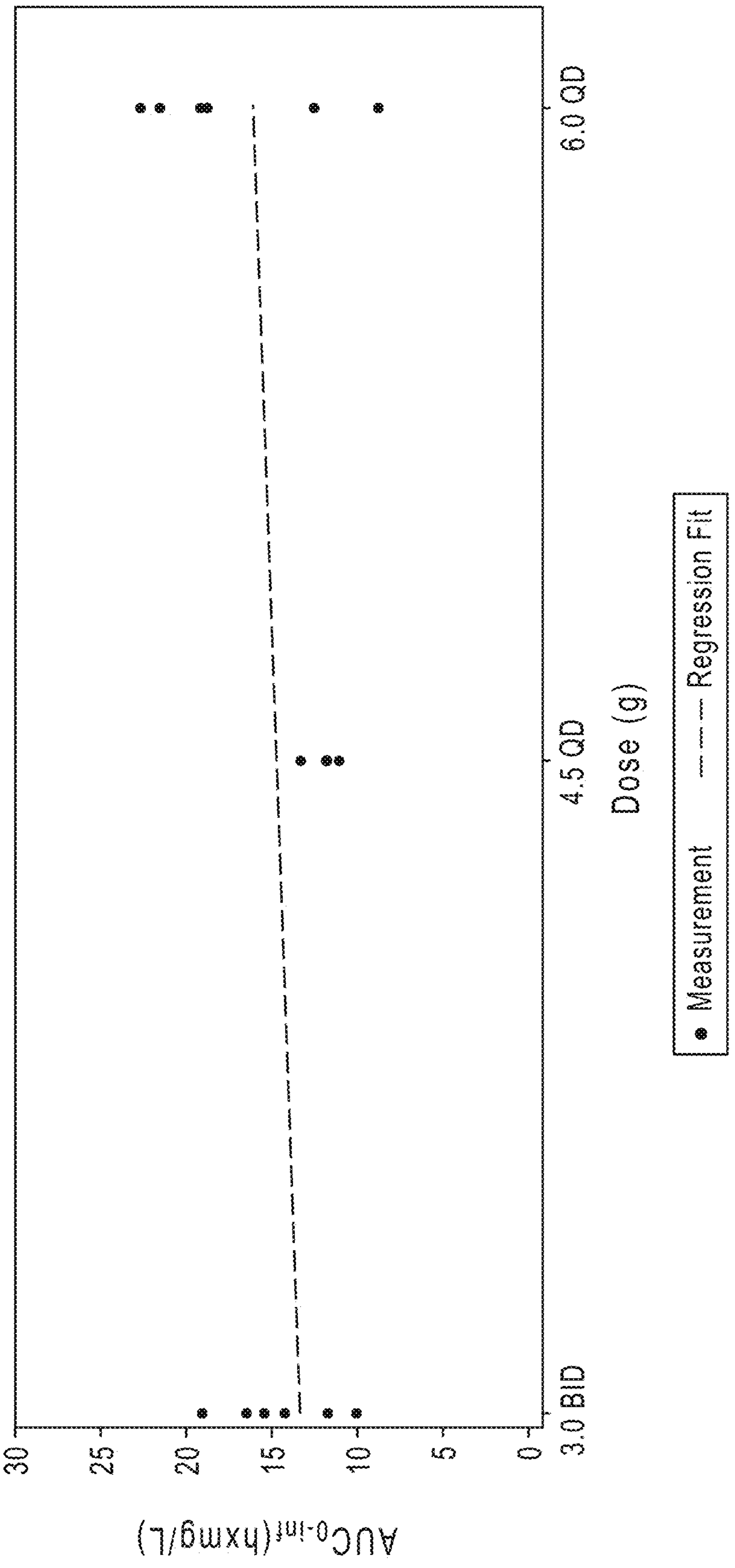
FIG. 11 shows the γ-hydroxybutyric acid plasma $AUC_{0\text{-}inf}$ following oral administration of different doses and dosing regimens of Compound (1) to healthy subjects.
Figure 12:
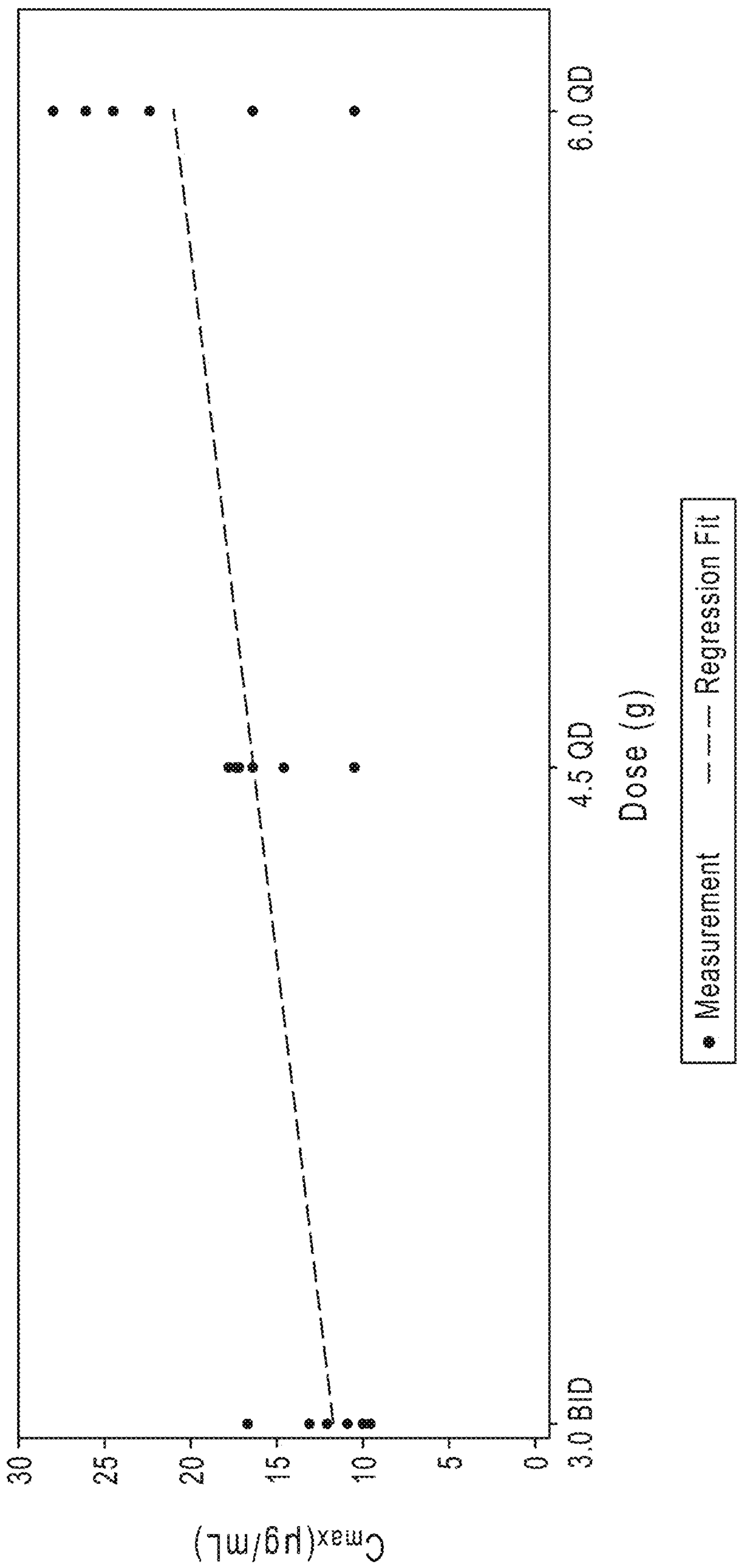
FIG. 12 shows the γ-hydroxybutyric acid plasma $C_{max}$ following oral administration of different doses and dosing regimens of Compound (1) to healthy subjects.

The mean plasma Compound (1) $AUC_{0\text{-}inf}$ (h×mg/L) and the mean plasma Compound (1) $C_{max}$ (mg/L) at Day 4 is shown in FIGS. 11 and 12, respectively.

Selected pharmacokinetic parameters for plasma GHB concentrations for Cohorts 8, 9, and 10 are shown in Tables 13, 14, and 15, respectively.

TABLE 13

Selected PK parameters for plasma GHB concentration for Cohort 8 (6.0 g/day divided into 2 equal doses).

| Dosing Day | Statistic | $t_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) |
|---|---|---|---|---|---|---|
| 1 | N | 6 | 6 | 6 | 6 | 6 |
| | Mean | 0.56 | — | 39.9 | 85 | 86 |
| | SD | 0.28 | — | 10.6 | 25 | 24 |
| | Min | 0.35 | 0.50 | 27.8 | 60 | 61 |
| | Median | 0.49 | 0.75 | 40.5 | 82 | 83 |
| | Max | 1.08 | 4.75 | 56.3 | 131 | 132 |
| 7 | N | 5 | 6 | 6 | 6 | 5 |
| | Mean | 0.39 | — | 39.2 | 86 | 87 |
| | SD | 0.09 | — | 10.8 | 26 | 29 |
| | Min | 0.32 | 0.50 | 27.1 | 65 | 65 |
| | Median | 0.39 | 0.75 | 36.9 | 80 | 74 |
| | Max | 0.53 | 4.75 | 54.8 | 136 | 136 |

TABLE 14

Selected PK parameters for plasma GHB concentration for Cohort 9 (4.5 g/day in a single dose).

| Dosing Day | Statistic | $t_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) |
|---|---|---|---|---|---|---|
| 1 | N | 6 | 6 | 6 | 6 | 6 |
| | Mean | 0.67 | — | 70 | 132 | 133 |
| | SD | 0.28 | — | 20 | 44 | 44 |
| | Min | 0.36 | 0.45 | 51 | 67 | 67 |
| | Median | 0.65 | 0.62 | 61 | 126 | 127 |
| | Max | 1.18 | 1.00 | 99 | 197 | 198 |
| 7 | N | 6 | 6 | 6 | 6 | 6 |
| | Mean | 0.63 | — | 76 | 127 | 128 |
| | SD | 0.14 | — | 16 | 41 | 42 |
| | Min | 0.40 | 0.75 | 60 | 60 | 61 |
| | Median | 0.66 | 0.75 | 70 | 128 | 128 |
| | Max | 0.776 | 1.00 | 101 | 176 | 178 |

TABLE 15

Selected PK parameters for plasma GHB concentration for Cohort 10 (6.0 g/day in a single dose).

| Dosing Day | Statistic | $t_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) |
|---|---|---|---|---|---|---|
| 1 | N | 6 | 6 | 6 | 6 | 6 |
| | Mean | 0.68 | — | 70 | 141 | 141 |
| | SD | 0.20 | — | 16 | 76 | 76 |
| | Min | 0.40 | 0.50 | 46 | 57 | 58 |
| | Median | 0.64 | 0.75 | 72 | 122 | 123 |
| | Max | 0.93 | 0.75 | 88 | 268 | 269 |
| 7 | N | 5 | 5 | 5 | 5 | 5 |
| | Mean | 0.48 | — | 69 | 122 | 123 |
| | SD | 0.08 | — | 23 | 73 | 73 |
| | Min | 0.40 | 0.50 | 42 | 54 | 54 |
| | Median | 0.44 | 0.75 | 69 | 91 | 91 |
| | Max | 0.58 | 1.00 | 103 | 232 | 233 |

Figure 13:
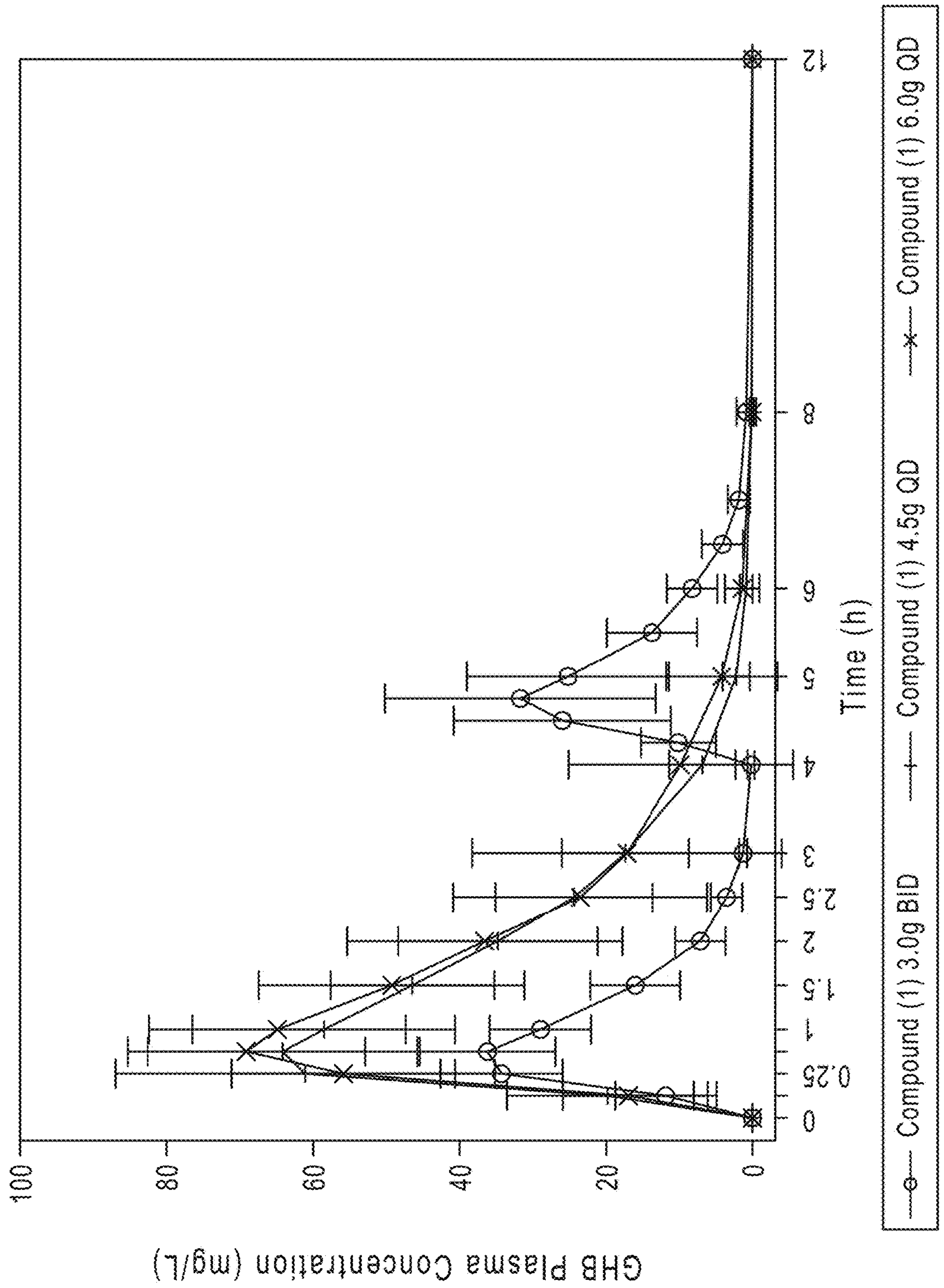
FIG. 13 shows the mean γ-hydroxybutyric acid plasma concentration following oral administration of twice a day dose ("BID") or for times a day doses ("QID") doses of Compound (1) to healthy subjects.
Figure 14:
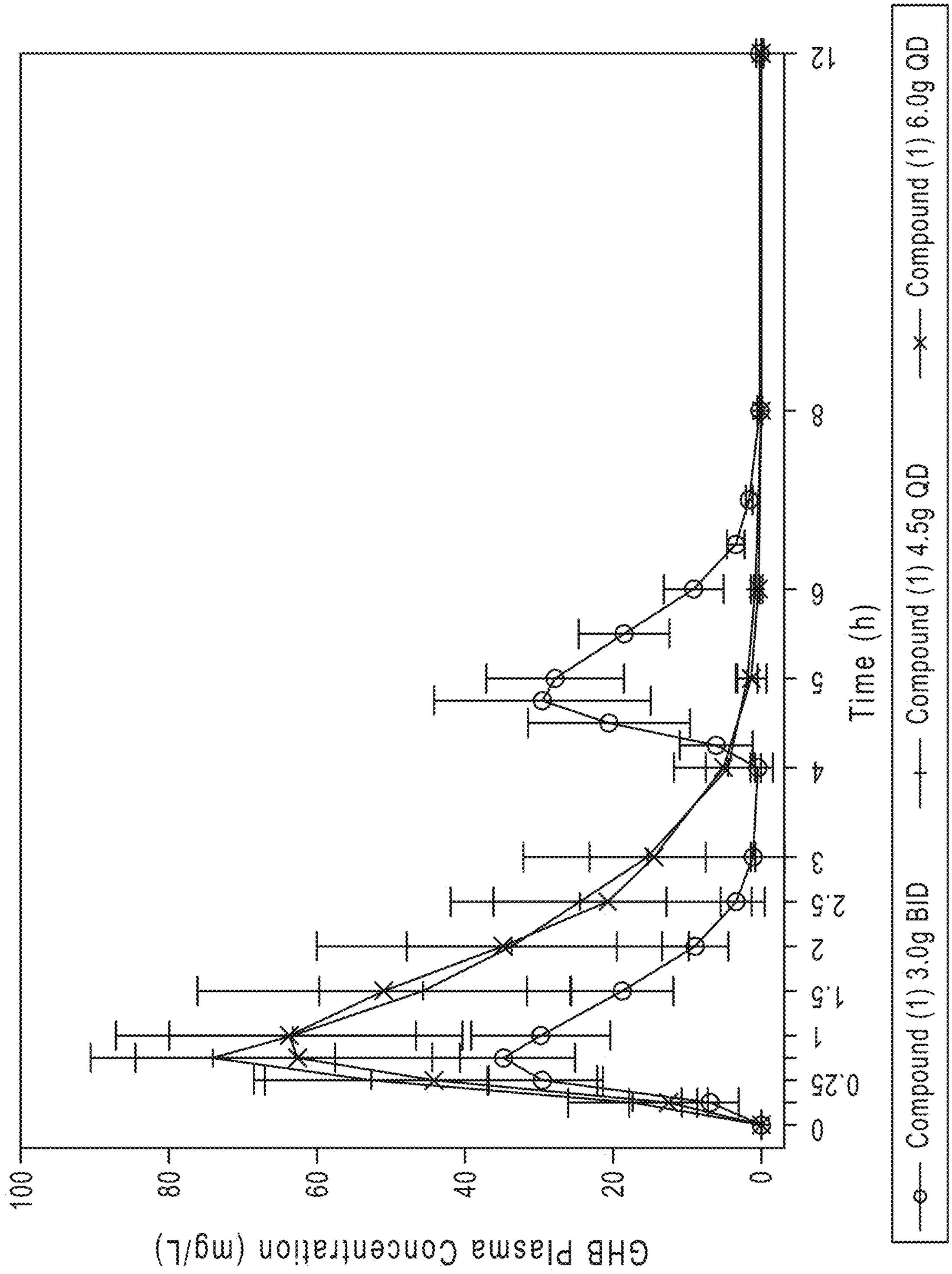
FIG. 14 shows the mean γ-hydroxybutyric acid plasma concentration following oral administration of BID or QID doses of Compound (1) to healthy subjects.

Pharmacokinetic profiles of the mean plasma GHB concentration (mg/L) for the three cohorts are shown in FIGS. 13 and 14 at Day 4 and at Day 10, respectively.

Example 4

Food Effect and Relative Bioavailability

An open-label, 4-period crossover study with 8 healthy subjects, was undertaken to evaluate the food effects on the pharmacokinetics of Compound (1) and GHB, and to determine the relative oral bioavailability of GHB derived from Compound (1) as compared to sodium oxybate at equal molar doses. Subjects were randomized into 1 of 4 dosing sequences: ABCD, BCDA, CDAB, and DABC, with 2 subjects per sequence. In each dosing sequence, the subjects received a single oral dose of either Compound (1) or sodium oxybate in 1 of 4 dosing modes (Compound (1) fed or fasted at 7.25 g (3.7 gm-equivalents GHB), sodium oxybate fed or fasted at 4.5 g (3.7 gm-equivalents GHB)). The subjects fasted for 4 hours post-dose.

Each single dose (aqueous solution) administered in the morning was accompanied by 60 mL of water.

The treatment conditions are summarized in Table 16.

TABLE 16

Treatment conditions for the evaluation of the pharmacokinetics of plasma GHB concentration following administration of Compound (1) and Na-oxybate.

| Treatment | Dose of Compound (1) | Dose of Na-oxybate | Conditions |
|---|---|---|---|
| A | 7.25 g (72.5 mL) | — | Fasted (for 10 h) |
| B | 7.25 g (72.5 mL) | — | Fed (following a standard breakfast) |
| C | — | 4.5 g (60 mL) | Fasted (for 10 h) |
| D | — | 4.5 g (60 mL) | Fed (following a standard breakfast) |

The pharmacokinetic profiles for the mean Compound (1) plasma concentration (mg/L) following oral administration of Compound (1) are shown in FIG. 15.

Selected pharmacokinetic parameters for Compound (1) following oral administration of 7.25 g Compound (1) to health subjects is shown in Table 17.

TABLE 17

Selected PK parameters for plasma Compound (1) concentrations following administration of Compound (1) (7.25 g) to healthy fasted and fed subjects.

| Food Status | Statistic | $T_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) |
|---|---|---|---|---|---|---|
| Fasted | N | 7 | 8 | 8 | 8 | 7 |
| | Mean | 0.54 | — | 27.7 | 23.9 | 22.4 |
| | SD | 0.59 | — | 10.7 | 8.3 | 7.3 |
| | Min | 0.27 | 0.25 | 9.4 | 9.4 | 9.5 |
| | Median | 0.35 | 0.75 | 27.3 | 22.5 | 20.4 |
| | Max | 1.90 | 0.75 | 43.6 | 36.1 | 30.8 |
| Fed | N | 8 | 8 | 8 | 8 | 8 |
| | Mean | 0.64 | — | 18.1 | 28.8 | 29.0 |
| | SD | 0.30 | — | 7.0 | 7.6 | 7.67 |
| | Min | 0.27 | 0.25 | 5.5 | 15.9 | 16.0 |
| | Median | 0.59 | 0.50 | 17.3 | 29.0 | 29.1 |
| | Max | 1.15 | 1.50 | 27.8 | 38.6 | 39.0 |

The pharmacokinetic profiles for the mean GHB plasma concentration (mg/L) following oral administration of either Compound (1) or sodium oxybate are shown in FIG. 16.

TABLE 18

Selected PK parameters for plasma GHB concentration following administration of equal molar GHB doses as Compound (1) (7.25 g) and sodium oxybate (4.5 g).

| Food Status Compound (amount) | Statistic | $T_{1/2}$ (h) | $T_{max}$ (h) | $C_{max}$ (μg/mL) | $AUC_{0\text{-}tlast}$ (h × μg/mL) | $AUC_{0\text{-}inf}$ (h × μg/mL) |
|---|---|---|---|---|---|---|
| Fasted Compound (1) (7.25 g) | N | 8 | 8 | 8 | 8 | 8 |
| | Mean | 0.77 | — | 122 | 348 | 352 |
| | SD | 0.27 | — | 33 | 161 | 164 |
| | Min | 0.39 | 0.50 | 68 | 194 | 197 |
| | Median | 0.70 | 1.00 | 124 | 295 | 297 |
| | Max | 1.25 | 1.05 | 180 | 635 | 647 |
| Fed Compound (1) (7.25 g) | N | 8 | 8 | 8 | 8 | 8 |
| | Mean | 0.81 | — | 76 | 274 | 282 |
| | SD | 0.29 | — | 26 | 140 | 147 |
| | Min | 0.42 | 0.75 | 43 | 102 | 103 |
| | Median | 0.78 | 1.75 | 73 | 256 | 262 |
| | Max | 1.30 | 2.50 | 107 | 498 | 519 |
| Fasted Na-oxybate (4.5 g) | N | 8 | 8 | 8 | 8 | 8 |
| | Mean | 0.76 | — | 146 | 344 | 349 |
| | SD | 0.31 | — | 26 | 120 | 127 |
| | Min | 0.47 | 0.25 | 109 | 234 | 234 |
| | Median | 0.62 | 0.50 | 147 | 314 | 318 |
| | Max | 1.39 | 1.00 | 193 | 550 | 577 |
| Fed Na-oxybate (4.5 g) | N | 7 | 7 | 7 | 7 | 7 |
| | Mean | 0.67 | — | 81 | 273 | 277 |
| | SD | 0.25 | — | 26 | 124 | 130 |
| | Min | 0.39 | 0.50 | 58 | 150 | 151 |
| | Median | 0.60 | 1.50 | 72 | 270 | 271 |
| | Max | 1.18 | 3.00 | 122 | 528 | 547 |

The relative bioavailability of GHB following oral administration of equimolar GHB doses of Compound (1) (7.25 g) and sodium-oxybate (4.5 g) to healthy fasted subjects are provided in Table 19.

TABLE 19

Assessment of relative bioavailability between equal molar GHB doses as Compound (1) (7.25 g) or sodium oxybate (4.5 g) administered to healthy fasted subjects.

| PK | | N (n) | | Adjusted Geometric Mean | | Adjusted | 90% |
|---|---|---|---|---|---|---|---|
| Parameter (unit) | Treatment Comparison | Cmpd (1) | Na-Oxybate | Cmpd (1) | Na-Oxybate | Geometric Mean Ratio | Confidence Interval |
| $AUC_{0\text{-}tlast}$ (h × μg/mL) | Compound (1) Na-oxybate | 8 (8) | 8 (8) | 320 | 328 | 0.98 | (0.89, 1.08) |
| $AUC_{0\text{-}inf}$ (h × μg/mL) | Compound (1) Na-oxybate | 8 (8) | 8 (8) | 324 | 332 | 0.98 | (0.89, 1.08) |
| $C_{max}$ (μg/mL) | Compound (1) Na-oxybate | 8 (8) | 8 (8) | 118 | 144 | 0.82 | (0.71, 0.94) |

Selected pharmacokinetic parameters for plasma GHB concentration following oral administration of either 7.25 g Compound (1) or 4.5 g sodium oxybate (both corresponding to 3.7 gm-equivalents of GHB to healthy subjects is shown in Table 18.

The relative oral bioavailability of GHB following oral administration of equimolar GHB doses of Compound (1) (7.25 g) and sodium-oxybate (4.5 g) to healthy fed subjects are provided in Table 20.

TABLE 20

Assessment of relative bioavailability between equal molar GHB doses derived from Compound (1) (7.25 g) or sodium oxybate (4.5 g) in healthy fed subjects.

| PK Parameter (unit) | Treatment Comparison | N (n) Cmpd (1) | N (n) Na-Oxybate | Adjusted Geometric Mean Cmpd (1) | Adjusted Geometric Mean Na-Oxybate | Adjusted Geometric Mean Ratio | 90% Confidence Interval |
|---|---|---|---|---|---|---|---|
| $AUC_{0\text{-}tlast}$ (h × μg/mL) | Compound (1) Na-oxybate | 8 (7) | 8 (7) | 226 | 259 | 0.87 | (0.78, 0.97) |
| $AUC_{0\text{-}inf}$ (h × μg/mL) | Compound (1) Na-oxybate | 8 (7) | 8 (7) | 230 | 261 | 0.88 | (0.79, 0.98) |
| $C_{max}$ (μg/mL) | Compound (1) Na-oxybate | 8 (7) | 8 (7) | 73 | 82 | 0.89 | (0.77, 1.03) |

An assessment of the food effect on the plasma Compound (1) concentration following oral administration of 7.25 g Compound (1) to healthy subjects is provided in Table 21.

TABLE 21

Assessment of food effect on plasma Compound (1) concentrations.

| PK Parameter (unit) | Treatment Comparison | N (n) Fed | N (n) Fasted | Adjusted Geometric Mean Fed | Adjusted Geometric Mean Fasted | Adjusted Geometric Mean Ratio | 90% Confidence Interval |
|---|---|---|---|---|---|---|---|
| $AUC_{0\text{-}inf}$ (h × mg/L) | Compound (1) (Fed vs Fasted) | 8 (7) | 8 (7) | 27.0 | 21.0 | 1.28 | (1.09, 1.52) |
| $C_{max}$ (μg/mL) | Compound (1) (Fed vs Fasted) | 8 (8) | 8 (8) | 16.5 | 25.4 | 0.65 | (0.57, 0.74) |

An assessment of the food effect on the plasma GHB concentration following oral administration of 7.25 g Compound (1) to healthy subjects is provided in Table 22.

TABLE 22

Assessment of food effect on plasma GHB concentrations.

| PK Parameter (unit) | Treatment Comparison | N (n ) Fed | N (n ) Fasted | Adjusted Geometric Mean Fed | Adjusted Geometric Mean Fasted | Adjusted Geometric Mean Ratio | 90% Confidence Interval |
|---|---|---|---|---|---|---|---|
| $AUC_{0\text{-}inf}$ (h × mg/L) | Compound (1) (Fed vs Fasted) | 8 (8) | 8 (8) | 250 | 324 | 0.77 | (0.67, 0.88) |
| | Na-oxybate (Fed vs, Fasted) | 8 (8) | 8 (8) | 253 | 332 | 0.76 | (0.62, 0.94) |
| $C_{max}$ (μg/mL) | Compound (1) (Fed vs, Fasted) | 8(8) | 8(8) | 72 | 118 | 0.61 | (0.52, 0.72) |
| | Na-oxybate (Fed vs, Fasted) | 8 (8) | 8 (8) | 79 | 144 | 0.55 | (0.50, 0.60) |

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. A pharmaceutical composition in the form of an aqueous solution comprising:

4-((L-valyl)oxy)butanoic acid; and malic acid, wherein the aqueous solution has a pH from 4.0 to 5.0 at a temperature of 25° C.; and wherein the aqueous solution has a concentration of the malic acid of from 4 g/mL to 8 g/mL.

2. The pharmaceutical composition of claim 1, wherein the aqueous solution has a concentration of 4-((L-valyl)oxy) butanoic acid of from 80 mg/mL to 120 mg/mL.

3. The pharmaceutical composition of claim 1, wherein the aqueous solution comprises from 2 g to 20 g of 4-((L-valyl)oxy)butanoic acid.

4. The pharmaceutical composition of claim 1, wherein the pharmaceutical composition comprises from 6.5 g to 8.5 g of 4-((L-valyl)oxy)butanoic acid.

5. The pharmaceutical composition of claim 1, wherein the aqueous solution further comprises:

from 3 wt % to 7 wt % of a sweetening agent; and from 0.2 wt % to 0.6 wt % of a flavoring agent;

wherein wt % is based on the total weight of the non-aqueous constituents of the aqueous solution.

6. A pharmaceutical composition in the form of an aqueous solution comprising:

from 84 wt % to 90 wt % of 4-((L-valyl)oxy)butanoic acid;

from 6 wt % to 8 wt % of malic acid;

from 4 wt % to 6 wt % of sucralose; and from 0.3 wt % to 0.5 wt % of a flavoring agent;

wherein wt % is based on the total weight of the non-aqueous constituents of the aqueous solution; and wherein the total of all non-aqueous constituents of the aqueous solution is 100 wt %;

wherein the aqueous solution has a pH from 4.0 to 5.0 at a temperature of 25° C.; and wherein the aqueous solution has a concentration of the malic acid of from 4 g/mL to 8 g/mL.

7. The pharmaceutical composition of claim 1, wherein the aqueous solution comprises coated granules comprising 4-((L-valyl)oxy)butanoic acid.

8. A method of providing a therapeutically effective amount of γ-hydroxybutyric acid in the plasma of a patient, the method comprising orally administering to a patient in need thereof the pharmaceutical composition of claim 1.

9. The method of claim 8, wherein the pharmaceutical composition comprises from 2 g to 20 g of 4-((L-valyl)oxy) butanoic acid.

10. A method of treating a disease in a patient in need thereof, the method comprising orally administering the pharmaceutical composition of claim 1 to the patient, wherein the disease is selected from narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's disease, fatigue associated with multiple sclerosis, and fibromyalgia.

11. The method of claim 10, wherein the administering comprises administering once per day or twice per day.

* * * * *